US009962333B2

(12) United States Patent
Gaillard et al.

(10) Patent No.: US 9,962,333 B2
(45) Date of Patent: May 8, 2018

(54) TIMED RELEASE OF SUBSTANCES TO TREAT OCULAR DISORDERS

(71) Applicant: BOARD OF TRUSTEES OF NORTHERN ILLINOIS UNIVERSITY, Dekalb, IL (US)

(72) Inventors: Elizabeth Gaillard, Dekalb, IL (US); James Dillon, Dekalb, IL (US); Jason Friedrichs, Sycamore, IL (US); Tao Xu, Lisle, IL (US); Timothy J. Hagen, Lisle, IL (US); Devi Kalyan Karumanchi, Dekalb, IL (US)

(73) Assignee: Board of Trustees of Northern Illinois University, DeKalb, IL (US)

( * ) Notice: Subject to any disclaimer, the term of this patent is extended or adjusted under 35 U.S.C. 154(b) by 76 days.

(21) Appl. No.: 14/907,745

(22) PCT Filed: Aug. 14, 2014

(86) PCT No.: PCT/US2014/051134
§ 371 (c)(1),
(2) Date: Jan. 26, 2016

(87) PCT Pub. No.: WO2015/023884
PCT Pub. Date: Feb. 19, 2015

(65) Prior Publication Data
US 2016/0184222 A1 Jun. 30, 2016

Related U.S. Application Data

(60) Provisional application No. 61/866,810, filed on Aug. 16, 2013.

(51) Int. Cl.
*A61K 9/00* (2006.01)
*A61K 47/34* (2017.01)
*A61K 9/127* (2006.01)

(52) U.S. Cl.
CPC .......... *A61K 9/0051* (2013.01); *A61K 9/0048* (2013.01); *A61K 9/127* (2013.01); *A61K 9/1271* (2013.01); *A61K 47/34* (2013.01)

(58) Field of Classification Search
CPC .... A61K 9/0051; A61K 47/34; A61K 9/0048; A61K 9/127; A61K 9/1271
See application file for complete search history.

(56) References Cited

U.S. PATENT DOCUMENTS

| 9,040,079 | B2 * | 5/2015 | Albrecht | A61K 9/0051 424/450 |
| 2004/0071770 | A1 * | 4/2004 | Smith | A61K 8/14 424/450 |
| 2009/0285878 | A1 * | 11/2009 | Hope | A61K 9/127 424/450 |
| 2012/0135064 | A1 * | 5/2012 | Campbell | C07K 16/22 424/450 |
| 2012/0321719 | A1 * | 12/2012 | McDonnell | A61K 9/0051 424/497 |

FOREIGN PATENT DOCUMENTS

| CN | 102327223 | 1/2012 |
| WO | WO2011/011607 | 1/2012 |
| WO | WO2012/021107 | 2/2012 |

OTHER PUBLICATIONS

Int'l Search Report and Written Opinion issued in App. No. PCT/US14/51134 (2015).
Cevc et al., "Lipid vesicles and membrane fusion," *Advanced Drug Delivery Reviews*, 38: 207-232 (1999).
Hamai et al., "Effect of Average Phospholipid Curvature on Supported Bilayer Formation on Glass by Vesicle Fusion," *Biophysical Journal*, 90(4): 1241-1248 (2006).
Lin et al., "Injectable systems and implantable conduits for peripheral nerve repair," *Biomed. Mater.*, 7: 024102 (9pp) (2012).
Mawad et al., "Advances in Hydrogels Applied to Degenerative Diseases," *Current Pharmaceutical Design*, 18: 2558-2575 (2012).
Moscho et al. "Rapid preparation of giant unilamellar vesicles," *Proc. Natl. Acad. Sci. USA*, 93: 11443-11447 (1996).
Yoshina-Ishii et al., "General Method for Modification of Liposomes for Encoded Assembly on Supported Bilayers," *J. Am. Chem. Soc.*, 127: 1356-1357 (2005).

* cited by examiner

*Primary Examiner* — Snighda Maewall
(74) *Attorney, Agent, or Firm* — Barnes & Thornburg LLP; Alice O. Martin

(57) ABSTRACT

A system is disclosed for simple, non-invasive, sustained delivery of ophthalmic substances to the interior of the eye, for the prevention and treatment of eye diseases and conditions. Liposomes and inverted micelles are disclosed as suitable vehicles, and timed release of the substances is effected. Delivery methods include coating of a lens or injection into the eye.

3 Claims, 35 Drawing Sheets

Vit F liposomes – means particle diameter 356 nm (without extrusion).

<u>General liposome info</u>

100 µm fluorescein made by Kalgen excitation: 494 nm emission 521 nm

Tocopherol (Vit E like compound) naturally found

PEG (polyethylene glycol) → sol. form @ room temp (add tocopherol to PEG)

PC stored in – 70 but can be kept in fridge while working.

Cholesterol stored in fridge

Only organic solvent used = ethanol

Use 2 ml of ethanol to dissolve phospholipids.

10 ml
8:2:1:.1:.1
PC: Cholesterol : PEG : Vit 3: fluorescein → 412.3 g/mol
dissolved in ethanol 60,000 rpm 1 hour pellets dispersed in phosphate solution PEG: ~200 g/mol in $H_2O$    cholesterol: 386.7 g/mol   Vit E : 0.45 g/ml

FW = 430.72

PC - ~768 g/mol $\underline{40 \text{ mg}}$ x $\underline{\text{ 1g }}$ x $\underline{1 \text{ mol}}$ = 5.2 x $10^5$ mol pc
8:2:1:.1:.1           1      1000mg    768 g $\underline{5.2 \text{ mol PC}}$ x $\underline{2 \text{ ml chol}}$ x $\underline{386.7g}$ = $\underline{0.005 \text{ g}}$ x $\underline{1000 \text{ mg}}$ = 5 mg chol
         8 mol PC     mol        1         1 g $\underline{5.2 \times 10^5 \text{ mol PC}}$ x $\underline{1 \text{ molPEG}}$ x $\underline{\text{ 200 g }}$ x $\underline{1000 \text{ mg}}$ = 1.3 mg PEG
         1              8 mol PC   molPEG      1 g
                                x $\underline{1.0 \text{ g}}$ = $\underline{0.0013 \text{ ml}}$ x $\underline{\text{ 1L }}$
                                  1 ml        1         1000 ml .0013
$\underline{5.2 \times 10^5 \text{ mol PC}}$ x $\underline{.1 \text{ mol Vit E}}$ x $\underline{430.72 \text{ g}}$ x $\underline{\text{ML}}$ = 0.00029 = 1.3 µL PEG
         1              8 mol PC      mol        0.45 g   2.9 µL Vit E 0.29 µL $\underline{5.2 \times 10^5 \text{ mol PC}}$ x $\underline{.1 \text{ mol fl}}$ x $\underline{412.3 \text{ g}}$ = 0.000267 g = 0.28 mg
         1              8 mol PC   mol $\underline{6.5 \times 107 \text{ mol}}$ = $\underline{100 \text{ µmol}}$         $\underline{0.65 \text{ µM}}$ = $\underline{100 \text{ µM}}$
       x              L                       L           1L

Formation based on p. 13 calc.

8:2:1:0.1:0.1
PC: Cholesterol: PEG: Vit E: fluorescein
40 mg: 5 mg: 1.3 µL: 0.29 µL: 0.28 mg ⟶ dissolve 8ml nda $H_2O$ Dissolve in 1.5 ml ethanol    dissolve in 0.5 ml ethanol    6.7 ml of 100 µM fluorescein sol.

add together
40 mg = .049 g
5 mg = 0.005 g added lipid mixture stir for 15 min
ethanol injection @ RT stir for 2 min
extrusion used .1 filters

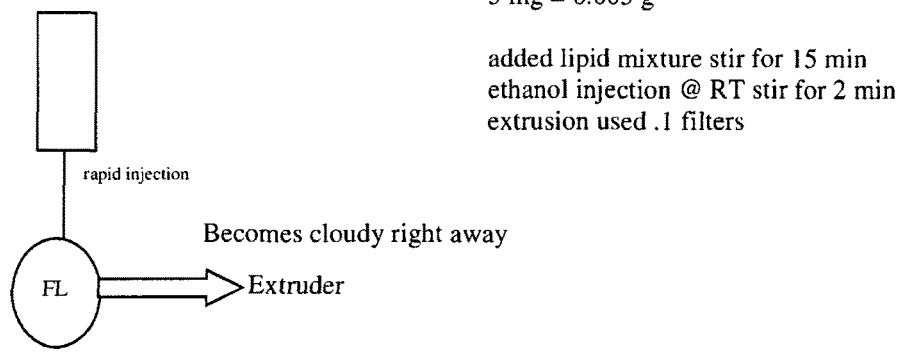

rapid injection

Becomes cloudy right away

FL ⟹ Extruder

Extruded 6 times until homogenous final V = 9.75 ml

To Do: Take UV FL of ethanol ⟶ 0
Sample $H_2O$ fluorescein $$\frac{0.0002g}{1} \times \frac{1 \text{ mol}}{412.3 \text{ g}} \times \frac{1}{0.008L} = 91\mu M$$

8:2:1:.1:.1
PC: cholesterol: PEG: Vit E: fluorescein 40 mg: 5 mg: 1.3 µl: 0.29 µl: [91 µM]

ethanol (1 ml)
ethanol (1 ml)
together stir 15 min ethanol injection @ room temperature
into 91 µM fluorescein use 1 ml into 10 ml add $H_2O$ after ethanol
injection solution
becomes cloudy
right away
indicating MLV stir 5 min @ room temperature
lipo mixture MLVs dry under air 30 min to get rid of
Extrude 10 x w/ 0.4V filters

FIG. 32(cont)

formation
Extruder mechanism
____ Hu base
Stainless steel support disk
Stainless steel mesh
poly drain disk + dd H$_2$O
Polycarbonate f Hu shiny side ↑
small O-ring
large O-ring
thermo barrel
large O-ring
Extruder top quick connect active from outlet \* pressure too high need fix N tank pressure gauge

FIG. 32(cont)

TIMED RELEASE OF SUBSTANCES TO TREAT OCULAR DISORDERS

CROSS REFERENCE TO RELATED APPLICATIONS

This application is a U.S. nationalization under 35 U.S.C. § 371 of International Application No. PCT/US2014/051134, filed Aug. 14, 2014, which claims priority to U.S. Provisional Application No. 61/866,810, filed Aug. 16, 2013. The disclosures set forth in the referenced applications are incorporated herein by reference in their entireties.

BACKGROUND

Materials and methods are presented to deliver liquids to the interior of the eye, in a timed release, to treat ocular diseases and conditions. Formulations for liposomes as vehicles for substances to coat contact lenses are described.

Currently, eye drops, applied externally, are used as a method to treat internal ocular disorders. However, this method suffers from the disadvantage that the liquid has to pass through many ocular bathers, many of which have opposite properties. For example; the epithelial layer of the cornea allows hydrophobic drugs to pass, whereas the stroma (the next layer) allows hydrophilic drugs to pass, not hydrophobic. In addition, lacrimation and impermeability through the corneal epithelium are responsible for poor ocular bioavailability.

Ocular diseases and conditions include age related macular degeneration (AMD), a common, chronic degenerative condition of the macula, which is a part of the retina. AMD is characterized by loss of central vision, whereas peripheral vision remains unaffected. Growth and leakage of new blood vessels beneath the retina cause permanent damage to the light-sensitive retinal cells which then die off and create blind spots in the central vision. Treatment options for AMD include intravitreal injection of steroids and macromolecules (direct injection of the drugs into the vitreous humor), a very unpleasant technique that requires multiple applications. Complications include: endophthalmitis (an inflammatory condition of the intraocular cavities), increased IOP (intraocular pressure), retinal detachment, and development of glaucoma and cataracts. Other ocular conditions that require treatment are cataracts and infections. Treatments would benefit from timed release systems.

Liposomes are a possible choice for sustained release ocular drug delivery because of their amphiphilic nature. But, the conventional liposomal formulations have several disadvantages. The first major problem is the stability and low shelf life. These can be attributed to the fact that the phospholipids which form these liposomes are highly prone to oxidation and hydrolysis. Also liposomes have a tendency to fuse together, increasing the particle size and further cause light scattering.

Another major problem with the liposomes is the encapsulation efficiency. This depends on the concentration of cholesterol used to stabilize the phospholipid bilayers. High concentration of cholesterol leads to very inflexible bilayers leading to very low encapsulation and very slow release. On the other hand, low concentration of cholesterol causes very high encapsulation but very fast release. So, in order to overcome these disadvantages, there is a need to engineer the liposomal formulations to have higher stability, very low drug leakage, high encapsulation and slow release of the drug. Currently, there are no groups that have been successful in obtaining a protein drug release over 40 days.

SUMMARY

The present disclosure is a pioneering work for understanding the structure of the liposomes in order to improve their stability as well drug release properties. Currently, encapsulating drugs in the liposomes for ocular drug delivery is not reported. The literature available attributes failures to lack of stability in the liposomes as well as several other factors mentioned above. Results disclosed herein are from experiments designed to understand the variations in the liposomes with change in compositions, addition of adjuvants, method of preparation, freeze thaw cycles, surface modifications. The best formulations were determined based on the particle size, encapsulation efficiency and the time of drug release. A variety of advanced methods—structural, spectroscopic, biophysical and biochemical assays were used. The present results are innovative, especially in the field of ocular drug delivery.

Liposomal formulations which are very stable and have a long shelf life are disclosed. This was achieved by modifying the method of preparation and including additives to prevent damage of liposomes due to oxidation and hydrolysis. Different batches of formulations were designed and carefully screened on the basis of particle size and percentage drug encapsulation in order to obtain the best results. From the preliminary data, 3 good formulations resulted which had optimum particle size and very slow release of about 35-45 days instead of 3-4 days. But, in order to further prolong the time of release, the surface of liposomes was modified by using PEG. This increased time of release to approximately 180-200 days in vitro. These formulations (compositions) are useful to encapsulate small drugs as well as macromolecules like proteins.

Knowledge of stable liposomes was used to encapsulate model protein (to replicate the encapsulation of anti-VEGF drugs like Lucentis® and Avastin®). But disclosed formulations have shown a drug release of about 4.5-5 months which is around 3 times slower release than reported by others. Thus, with this technology, instead of monthly intravitreal injections @ 2500$/injection, the frequency of injections can be reduced to 3/year. The decrease in frequency of injections also decreases the chance of infections.

Further, coating the intraocular lenses with liposomes for treatment of endophthalmitis (bacterial and fungal infection) after cataract surgery is disclosed. Liposomes which release drug over 180-200 days are disclosed. In order to coat the liposomes onto the intraocular lens, an FDA approved biodegradable polymer PLGA is used which acts as a glue as well as a drug depot, and further extends the time of release of antibiotics; prevents infection for around 6 months. During this time, the eye develops its natural immunity and hence wards off any further infections.

In summary, very stable liposomal formulations with a slower drug release were developed. The technology described has a wide range of applications in ocular drug delivery for treating diseases especially endophthalmitis, diabetic retinopathy and wet age related macular degeneration. The formulations can be customized to treat ocular diseases as well. The advantage of this technology is effective treatment lower frequency as well as cost of doses.

BRIEF DESCRIPTION OF THE DRAWINGS

FIG. 32 provides General liposome information.

DETAILED DESCRIPTION

Materials and methods are described to directly deliver substances (drugs, medicines and medicaments) to the interior of the eye. The substances are designed to be slowly released over time (sustained, controlled, release) to treat diseases and conditions of the mammalian eye.

A timed release system to deliver substances or compositions to the interior of a mammalian eye is disclosed that includes:

(a) encapsulating vehicles; and
(b) encapsulating substances or compositions within the vehicles.

Suitable encapsulating vehicles include vesicles. The vehicles may be liposomes.

The substances encapsulated within the vehicles may be in the form of liquids or gels, and include drugs, medicaments or other treatments for diseases or conditions of the mammalian eye.

The diseases or conditions treated by the system include AMD, cataracts, dry eye, inflammation and infection.

A method of treating diseases of the mammalian eye is also disclosed:

(a) encapsulating substances to treat the eye; and
(b) delivering the encapsulated substances to the eye with controlled (sustained) release timer.

Sustained release (controlled, timed) delivery is achieved by manipulating the sizes of the encapsulating vehicles or the number of layers of the vehicles.

Compositions are also disclosed, embodiments of which include a liposome and an ocular drug or medicament encapsulated therein. These formulations are disclosed as examples.

Drugs are encapsulated in liposomes and then embedded in a coating material that is then applied onto an ocular device (e.g., intraocular lens or shunt). A coating applied to contact lenses, intraocular lens, or ocular stents includes substances to treat diseases or conditions of the eye. The substances include drugs, medicines, and medicaments, delivered by sustained release. The ocular device is then implanted in the eye to give controlled release of the drug over a specific period of time.

Suitable drugs include any small molecule (hydrophilic or hydrophobic) or peptides or proteins. For example, the liposome formulations provide the controlled release of e.g. Lucentis, or its equivalent, Avastin, drugs that are the only current treatment for "wet" AMD. These treatments are antibodies, that is proteins (large molecules). The antibodies are encapsulated in the liposomes and are directly injected as a solution into the posterior chamber of the eye. The drug is then controlled released. Note that the coating step may be omitted, and the encapsulated drugs directly injected into the eye rather than surgically implanting a device in the eye. Currently, ophthalmologists directly inject drugs as an ophthalmic solution, so injection has to be repeated e.g. every month. The disclosed materials and methods reduce the number of annual injections because of the controlled release.

Figure 1:
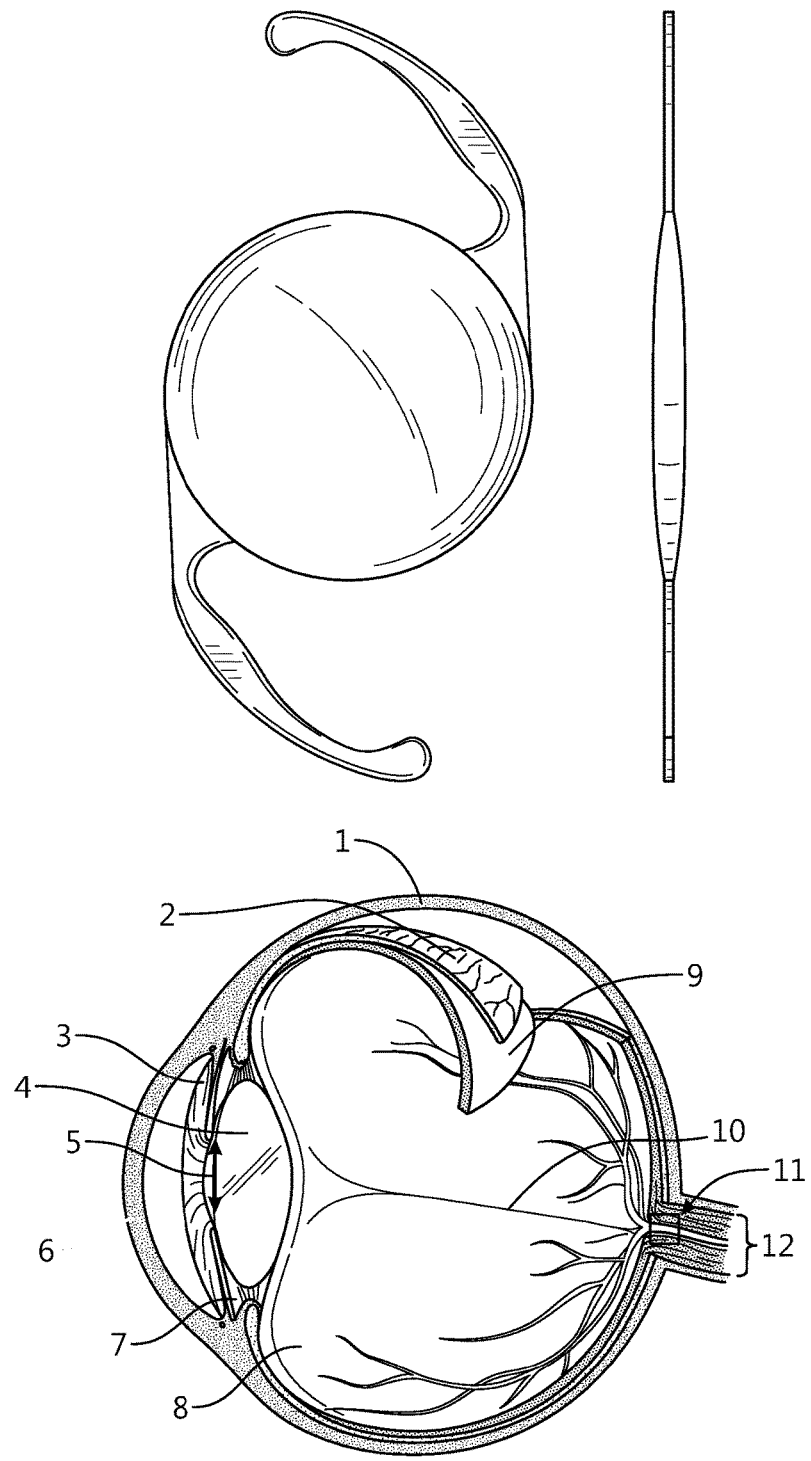
FIG. 1 shows a standard intraocular lens (IOL) which is placed in the space created in the eye when the natural lens is removed after cataract surgery and a diagram of a human eye.

In ophthalmology, there are several plastic devices that can be coated and act as vehicles to deliver various drugs. These include contact lenses and intraocular lenses (IOL), which are prosthetic lenses used after cataract surgery, as shown in FIG. 1. 1 is sclera, 2 is choroid, 3 is iris, 4 is lens, 5 is pupil, 6 is cornea, 7 is aqueous body, 8 is vitreous body, 9 is retina, 10 is fovea, 11 is optic disc (blind spot), 12 is optic nerve. An intraocular lens replaces the eye's natural lens after it is removed, e.g. during cataract surgery. The first FDA approval for IOL occurred in 1981.

The types of drugs that are imbedded in the plastic devices for the eye are those useful to treat dry eye, glaucoma, infection, and the like. Various drugs are encapsulated prior to delivery. The methods disclosed herein delay the loss of drugs from the vitreous and increase the effectiveness of the drugs.

Novel systems disclosed herein use inverted micelles for controlled and extended (sustained) delivery of substances (drugs, medicines and medicaments, e.g. antibiotics) across the retina. In an inverted micelle, the polar groups of the surfactants are concentrated in the interior of the micelle, and lipophilic groups extend towards the non polar solvent. The methods disclosed include three steps (1) encapsulating both hydrophilic and hydrophobic drugs into the inverted micelles and uni-lamellar liposomes; (2) incorporating these inverted micelles and liposomes into a hydrogel coating composite, or by covalently tethering the liposomes to the surface, to form a mixture; and (3) coating the mixture onto a contact lenses, IOL or ocular stint, for drug release. By manipulating the sizes of the encapsulating vehicles, controlled and extended release of therapeutic drugs is achieved. Because hydrogels are superabsorbent toward water, they maintain the integrity of the liposomes over long periods of time. Local application of encapsulated coated contact lenses or IOLs helps in the controlled time release of the drug to the target site.

Numerous different emulsions are suitable. These include liposomes and normal and reversed phase vesicles. These microheterogeneous systems can contain particles that are unilamellar (single-walled) or multilamellar (multi-layered) and the number of layers controls the release time of the encapsulated drug. Liposomes have the ability to encapsulate both hydrophilic and hydrophobic drugs, and deliver drugs to a specific site. Liposomes are bilayered, microscopic vesicles surrounded by aqueous compartments. The liposomes are made from naturally occurring phospholipids and fatty acids with stabilizers such as cholesterol. After drugs are encapsulated, the liposomes are then dispersed into a biocompatible polymer matrix such as cellulose that can then be coated onto a silicone surface. All of these materials are commercially available, e.g. Avanti Polar Lipids (Alabaster, Ala.) and biocompatible polymers (hydrogels) from Sigma-Aldrich (St. Louis, Mo.).

Materials and Methods

Figure 14:
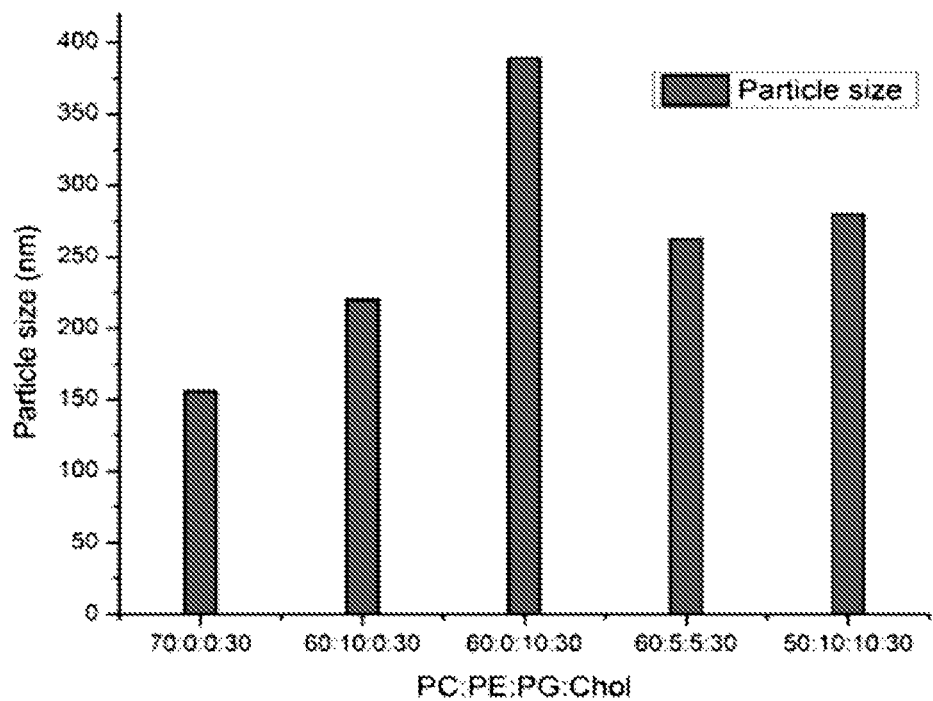
FIG. 14 shows results of investigations of the role of phospholipids on the stability of liposomes; particle size distribution.
Figure 15:
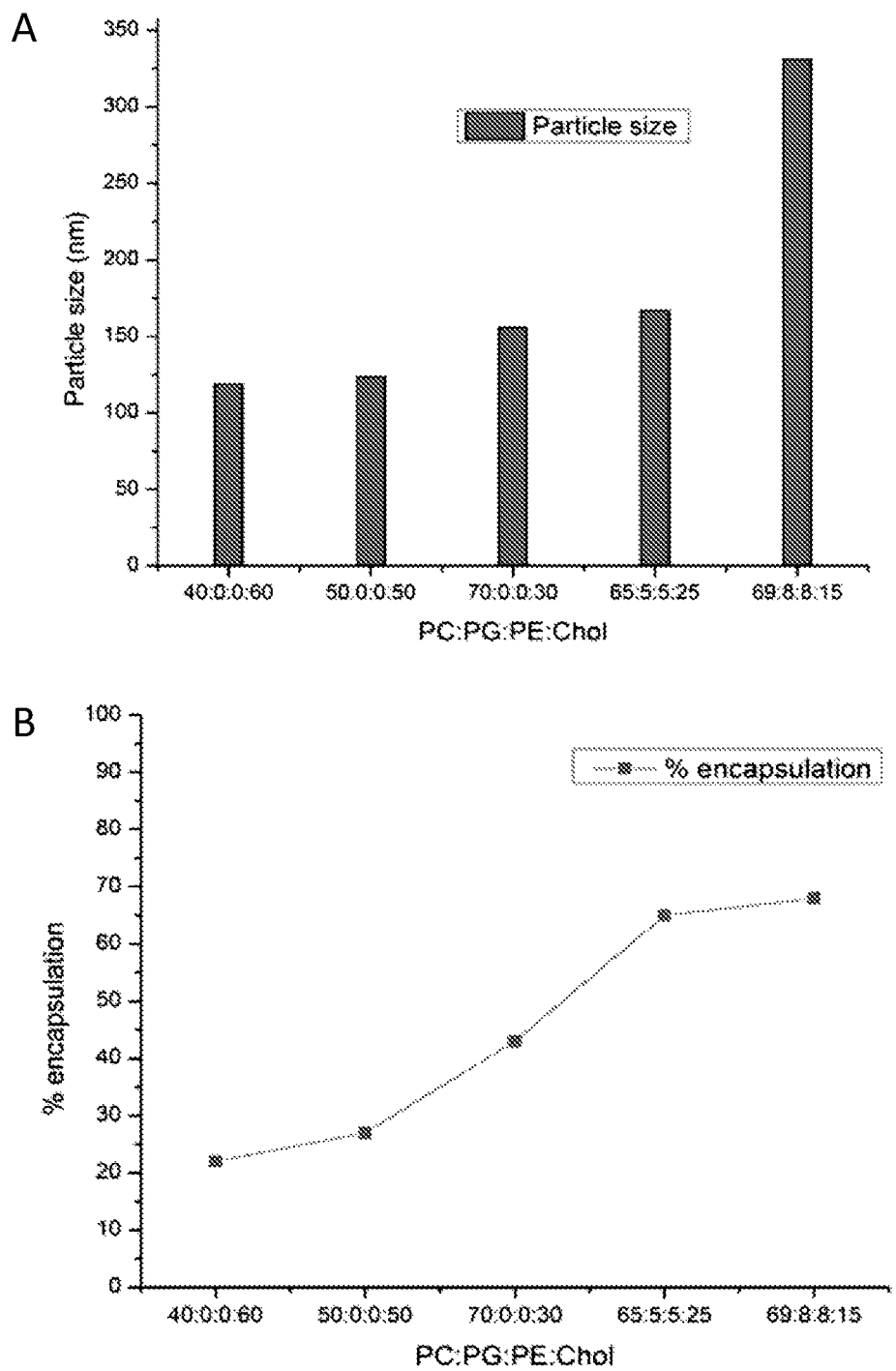
FIG. 15 shows results of investigations of the role of cholesterol on the stability of liposomes; (A) particle size distribution; (B) % encapsulation.
Figure 16:
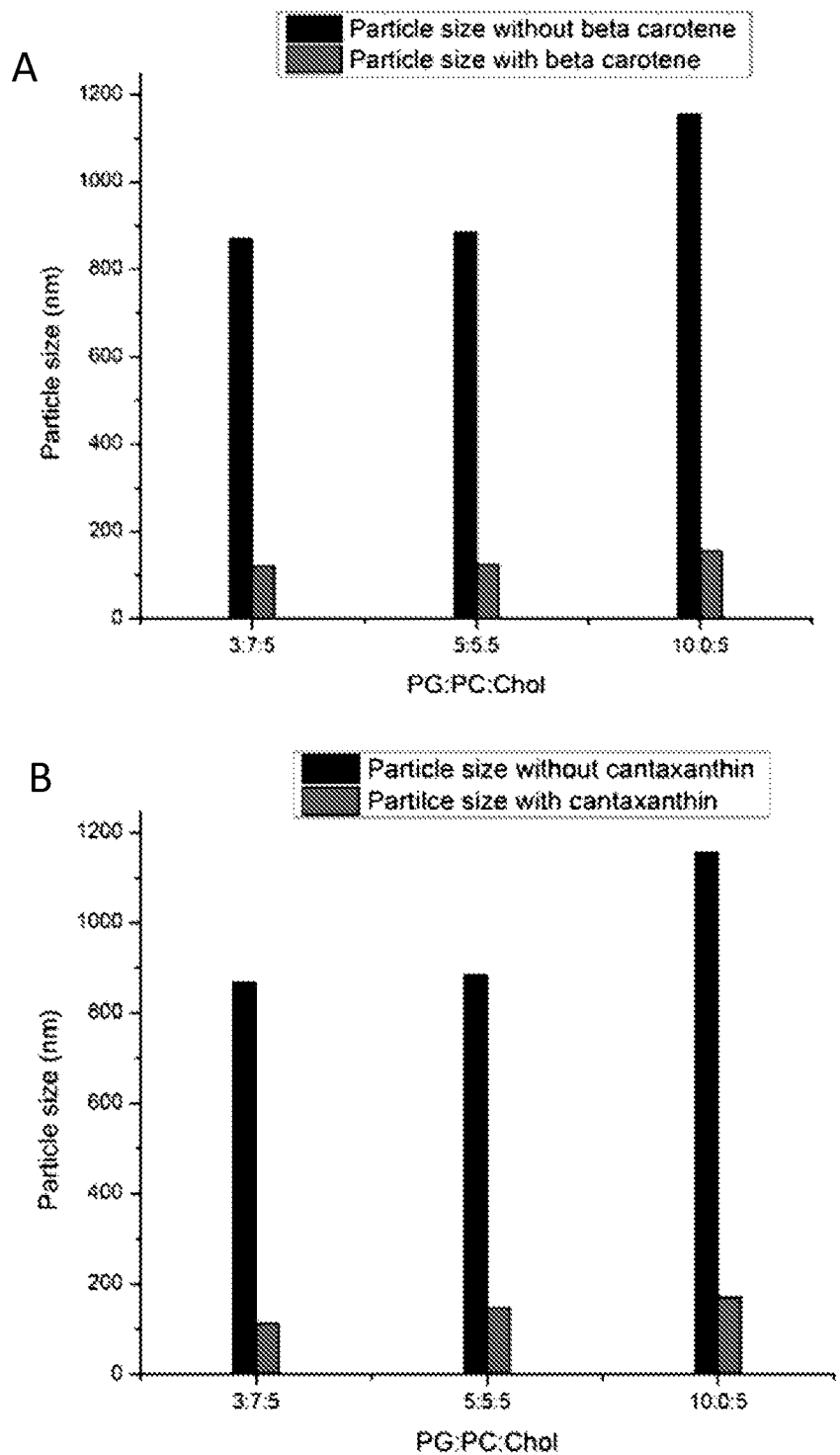
FIG. 16 shows results of investigation on the role of anti-oxidants on the stability of liposomes; (A) particle size distribution with or without beta carotene; (B) particle size distribution with or without cantaxanthin.

A. Pre-Formulation Investigations—Development of Methods for Obtaining Desired Formulations Results of investigations to determine the role of formulation (composition) variation, presence of adjuvants and methods of preparation on the structural stability of liposomes and their effects on drug release are disclosed, the roles of phospholipids, cholesterol, and anti-oxidants are shown in FIGS. 14, 15 and 16.

1. Role of Phospholipid Composition in the Stability of Liposomes: (FIG. 14)

The effect of lipid composition on the size and hence stability of the liposomes have been examined by preparing liposomes with different molar ratios of phospholipids. The molar ratio of cholesterol was kept constant. The liposomes with high concentrations of phosphatidyl choline were giving the optimum size of 100-200 nm. The compositions with high concentration of phosphatidyl glycerol were found to promote fusion and the overall increase in particle size. This can be attributed to the oxidation of unsaturated fatty acids on phosphatidyl glycerol. From this result, the lesser the concentration of phosphatidyl glycerol, the lesser the chance of oxidation of the liposomes, thereby, increasing the stability and shelf life.

2. Role of Cholesterol Composition in the Stability of Liposomes: (FIG. 15, A, B)

Dynamic light scattering (DLS) measurements of liposomes show that the ones with less cholesterol tend to be somewhat larger, on average, than liposomes with high cholesterol content. But in further studies, the higher concentration of cholesterol appeared to prevent the encapsulation of the encapsulated marker. So, an optimum concentration of cholesterol is required to have stable bilayers as well as optimum release. Use of 25-30 molar ratio of cholesterol gives very stable formulations.

3. Role of Anti-Oxidants in the Stability of Liposomes: (FIG. 16, A, B)

Cantaxanthin and Beta carotene were used as anti-oxidants to prevent the fusion of liposomes due to oxidation. A dramatic difference in the particle size of liposomes at different phospholipid and cholesterol concentrations in the presence and absence of the anti-oxidants is seen in the graphs: (FIG. 16, A, B)

4. Effect of Different Methods of Preparation on Liposomes

Conventional liposome preparation techniques were used to prepare the liposomes. The efficiency of these methods was determined based on the resulting particle size, encapsulation efficiency and the time of release of encapsulated marker (Fluorescein).

Figure 17:
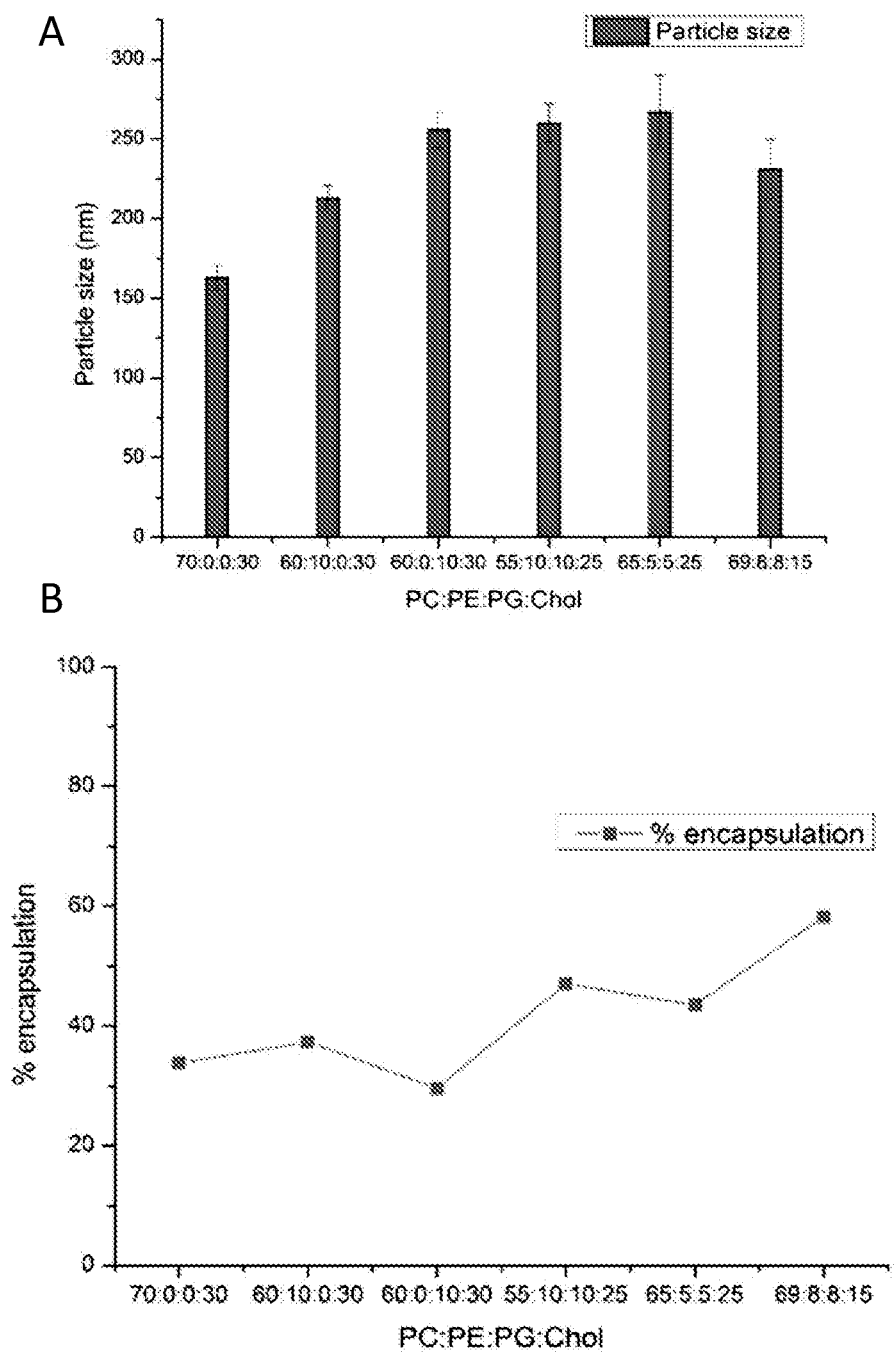
FIG. 17 shows effects of different methods of preparation on liposomes; lipid hydration and extrusion method: (A) particle size distribution; (B) % encapsulation.

(a) Lipid Hydration and Extrusion Method (FIG. 17, A, B)

Different combinations of phospholipids with or without cholesterol were mixed to total lipid concentration of 10 mM in chloroform-methanol mixture in ratio of 2:1. The mixture was rotovaped to get a thin film on the surface of the round bottom flask. The film was further flushed with argon for complete drying. Now, the lipid film was hydrated with the drug solution in phosphate buffer overnight. Finally the milky suspension was extruded using 0.4 and 0.2 μm polycarbonate filters.

Figure 18:
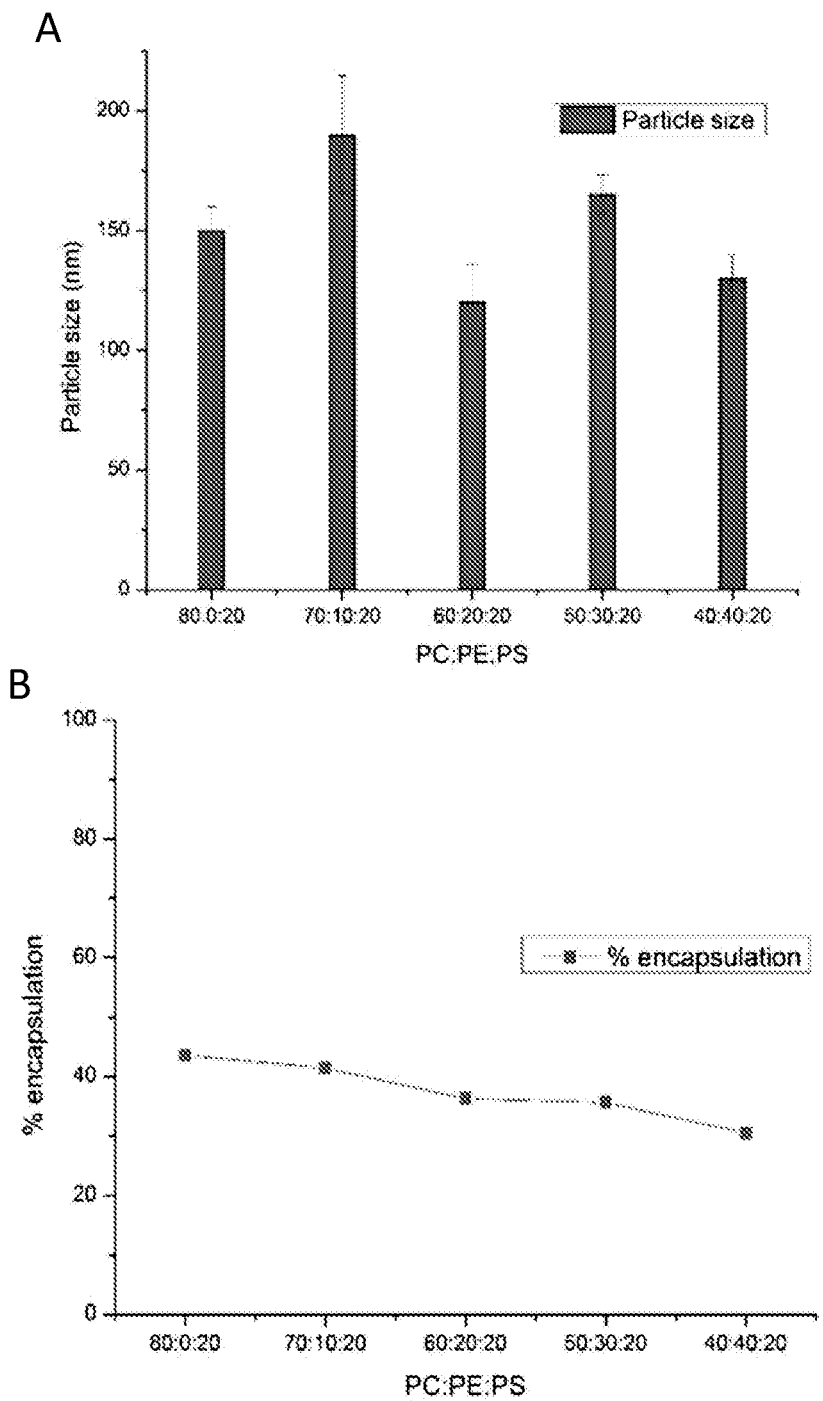
FIG. 18 shows effects of different methods of preparation on liposomes; sonication method; (A) particle size distribution; (B) % encapsulation.

(b) Sonication Method (FIG. 18, A, B)

Dispense 200 μl of 2.6 μM total phospholipids dissolved in chloroform in a glass test tube. Phosphatidyl choline and phosphatidyl serine are in the volume ratio of 4:1. The phospholipid mixture was dried under $N_2$ or Argon. Then, it is further dried under vacuum for an additional hr. To this film, 2.6 ml of HEPES buffer saline containing drug was added at room temperature. The dispersion was left to hydrate for 1 hr and vortexed to resuspend the pellet to get a milky suspension. The liposome solution was sonicated to get a clear solution.

Figure 19:
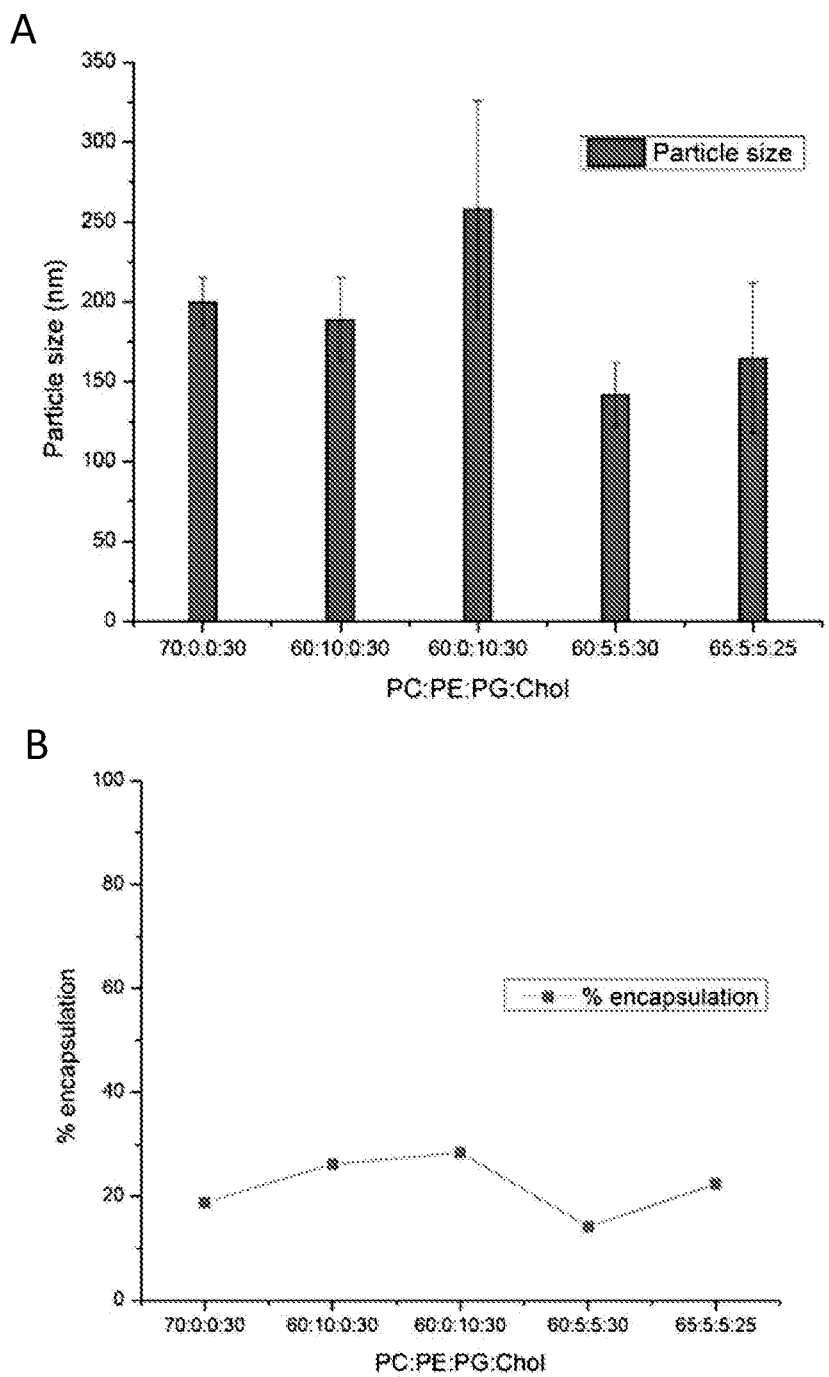
FIG. 19 shows effects of different methods of preparation on liposomes; reverse phase evaporation method; (A) particle size distribution; (B) % encapsulation.

(c) Reverse Phase Evaporation Method (FIG. 19, A, B)

Different combinations of PC-cholesterol were dissolved in 2:1 chloroform-methanol mixture. The solvents were evaporated off using a rotovap under vacuum at 40° C. The lipid film was re-dissolved in ether to produce reverse phase vesicles. 20 mg of drug was dissolved in acetone and 6 ml of PBS (pH 7.4). The system was sonicated for 4 min in a bath sonicator. The organic phase was then evaporated using a rotovap. The liposomes were allowed to equilibrate at room temperature and then 10 ml PBS was added to liposome suspension, which was refrigerated overnight.

Figure 20:
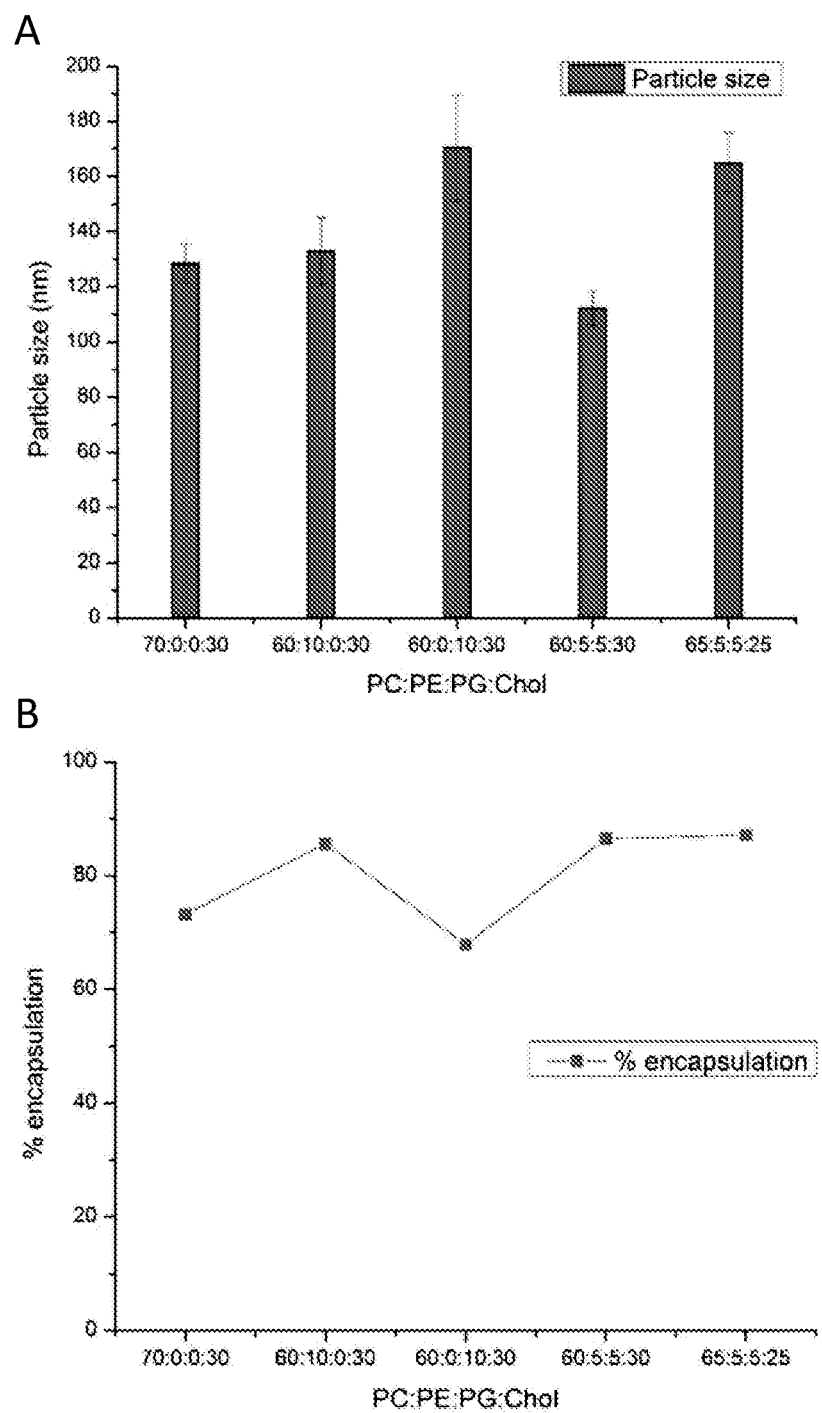
FIG. 20 shows effects of different methods of preparation on liposomes; cryo-protectant freeze thaw method; (A) particle size distribution; (B) % encapsulation.

(d) Cryo-Protectant Freeze Thaw Method (FIG. 20, A, B)

EPC, DPPE, DPPG and cholesterol were mixed at various molar ratios in a round bottom flask. To this, 2 ml of chloroform was added to make a uniform organic phase. The solvent was argon dried to get a uniform film of lipid layer. This lipid layer was hydrated using the protein solution in 0.32 M mannitol to get a final phospholipid concentration of 10 mg/ml. The dispersion was sonicated for 5 min in a bath sonicator. Now, the solution was frozen at −70° C. for 30 min and then thawed to 40° C. The process was repeated at least 6-7 times and the final sample was lyophilized after removal of excess protein.

Conclusion: The best 3 formulations were identified. Lipid hydration and extrusion method gave moderate encapsulation and optimum particle size. But, a problem was that the liposomes started to fuse. In case of mannitol freeze thaw method, the particle size was small and also the liposomes showed very good encapsulation. The problem with this method is that the liposomes leak the solute at a very fast rate due to osmotic imbalance inside and outside the liposomes. So, a modified method was used where both the lipid hydration and extrusion as well as the mannitol freeze thaw method were combined. Good particle size as well as very good encapsulation was achieved.

Figure 21:
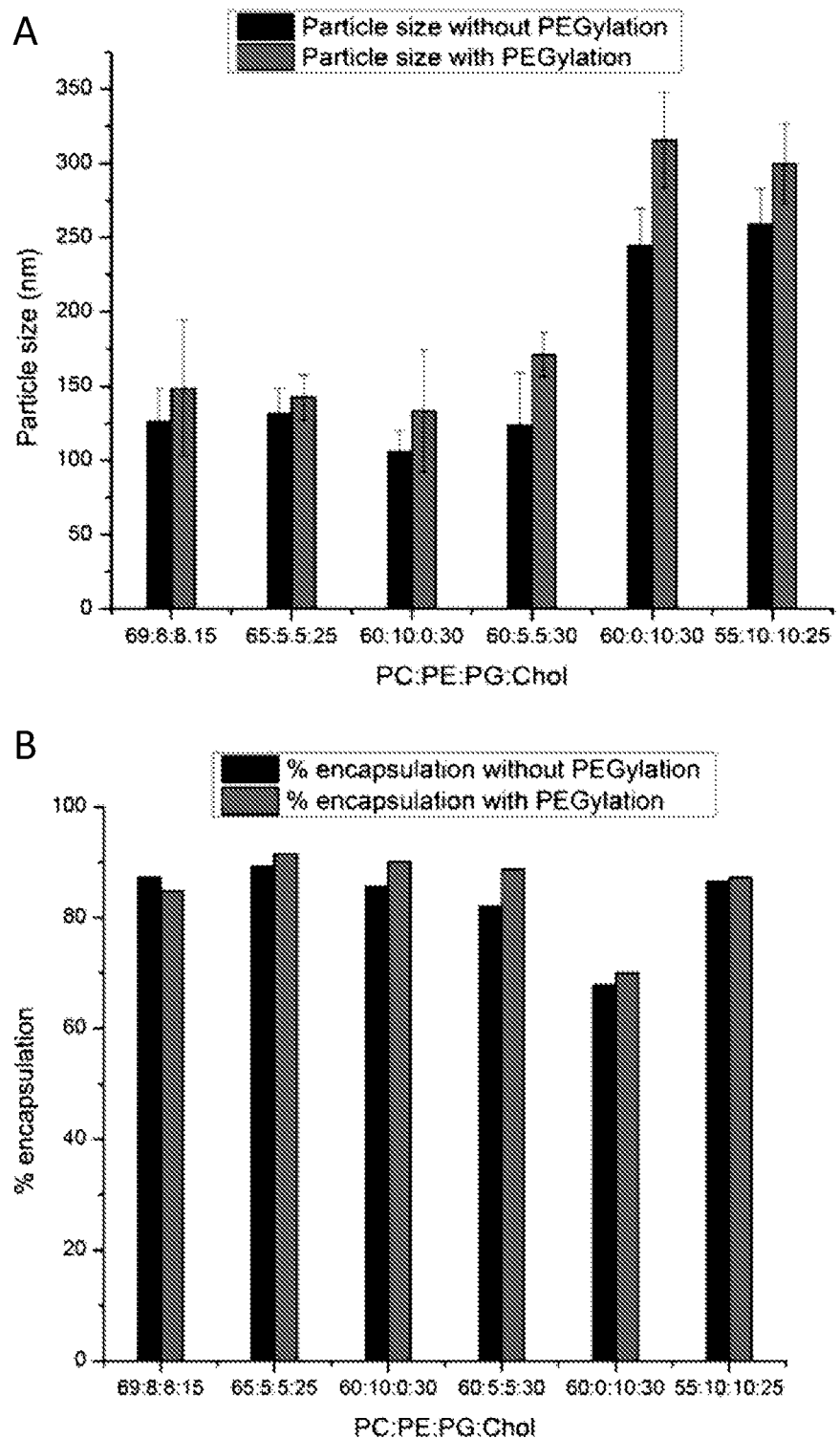
FIG. 21 shows effects of PEGylation on the stability of liposomes; (A) particle size distribution with and without PEGylation; (B) % encapsulation with and without PEGylation.

5. Effect of PEGylation on the Stability of Liposomes (FIG. 21, A, B)

PEGylation is a process for surface modification of the liposomes in order to increase the circulation time of the liposomes after being introduced into the host. The PEGylation process does not change the structure of the liposomes, but helps in preventing the leakage of drug encapsulated as well protects the liposomes from enzymatic degradation.

Figure 22A:
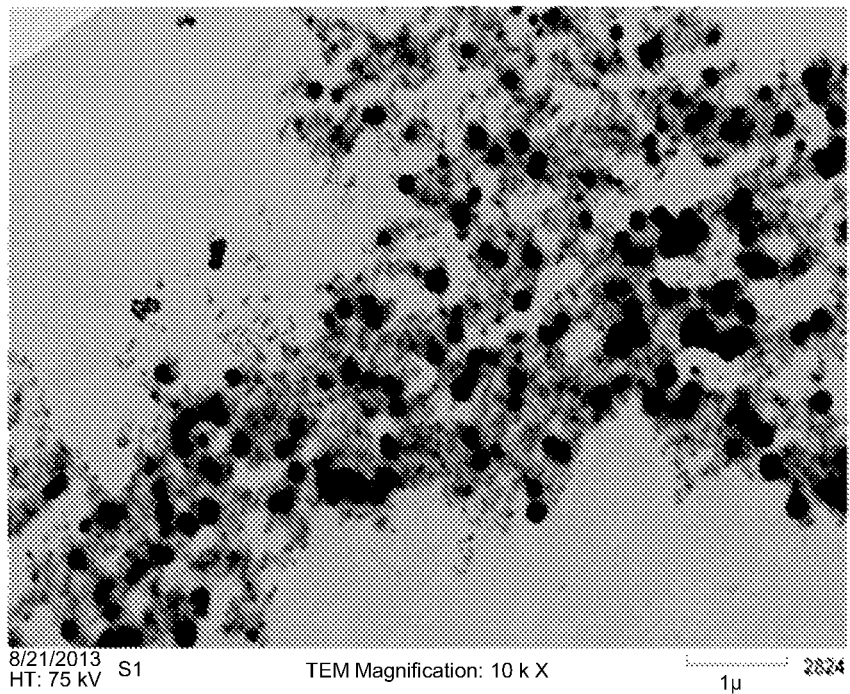
FIG. 22 shows TEM images of use of formulation on cells, using fluorescence as a marker for small molecules; (A) formulation 1; (B) formulation 2; (C) formulation 3.
Figure 22B:
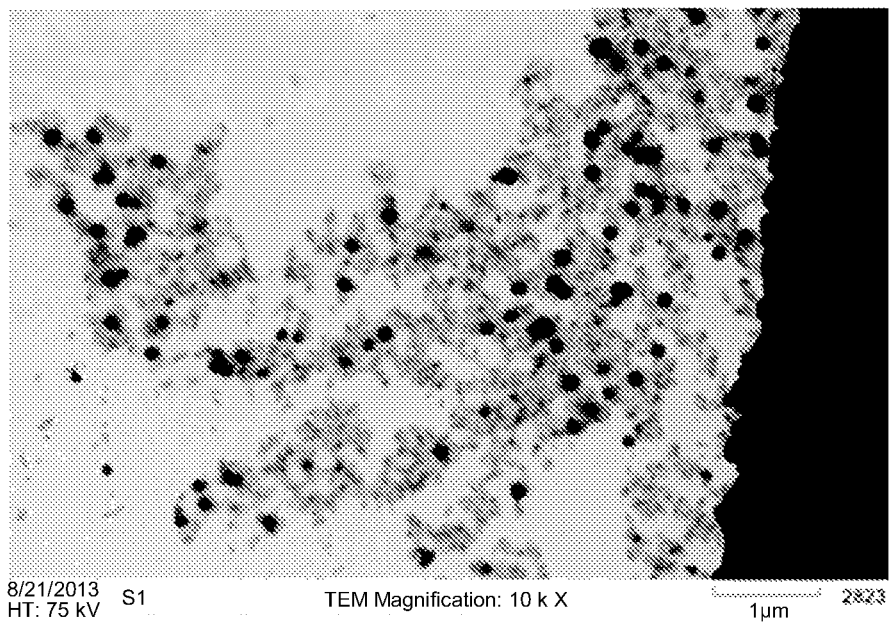
Figure 22C:
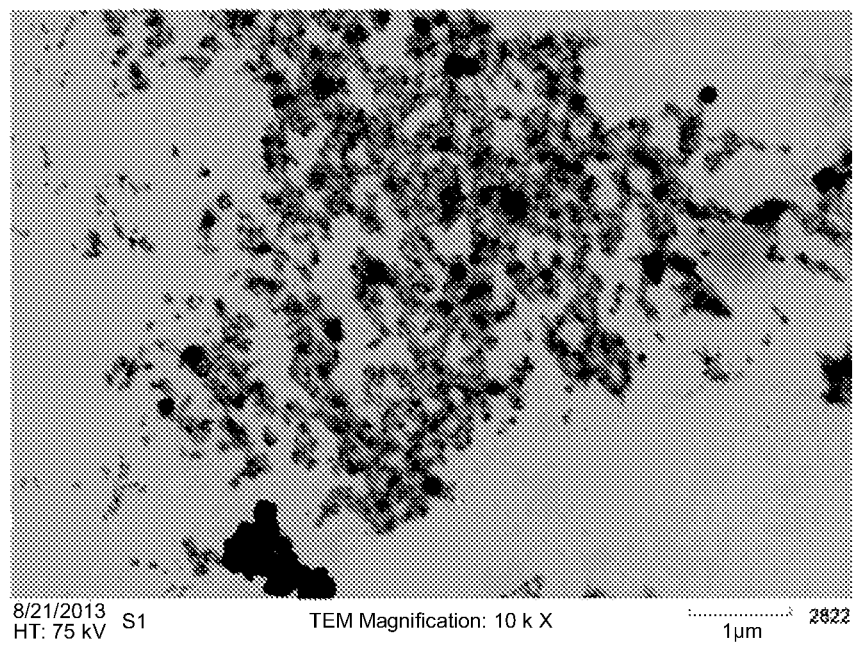

6. Fluorescein as a Model Marker for Small Molecules (TEM Images) (FIG. 22)

Figure 23A:
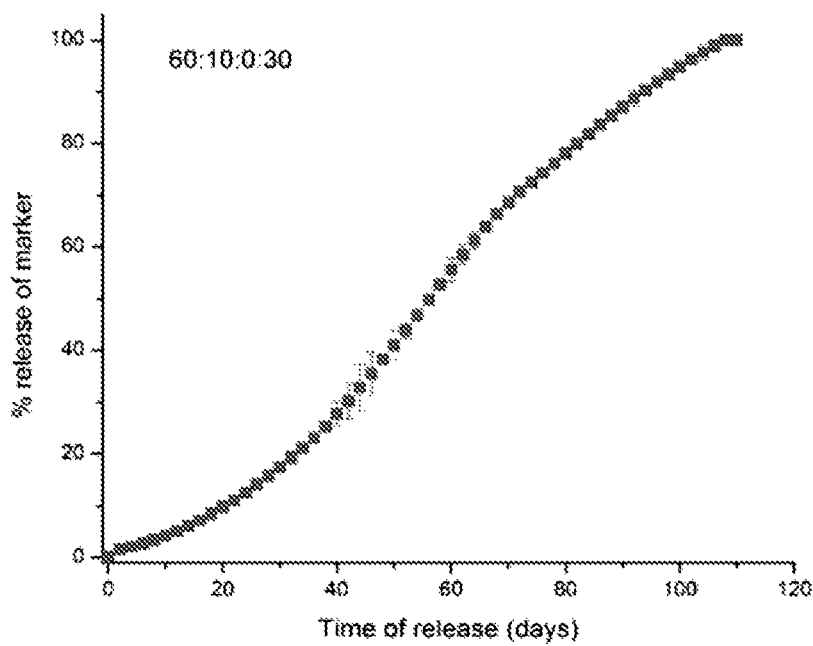
FIG. 23 shows time release curves for formulation (A) 1, (B) 2, (C) 3.
Figure 23B:
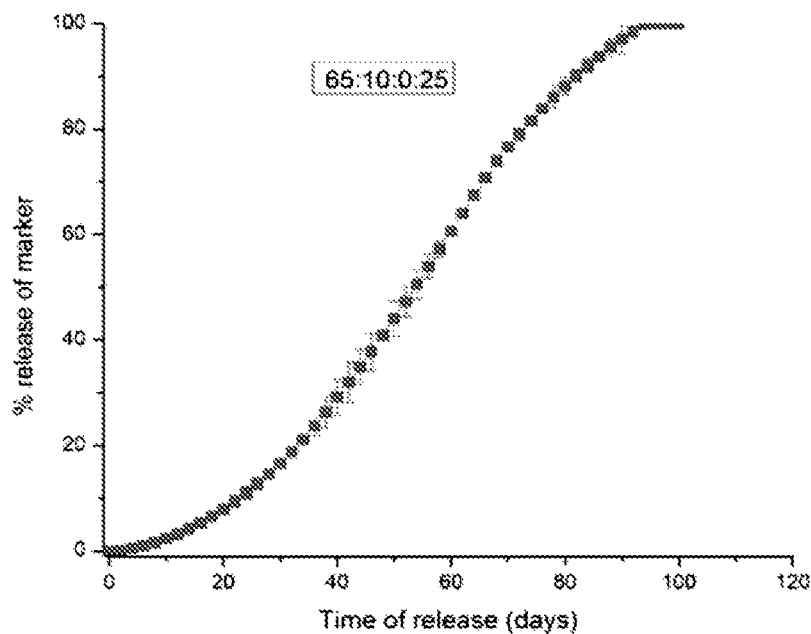
Figure 23C:
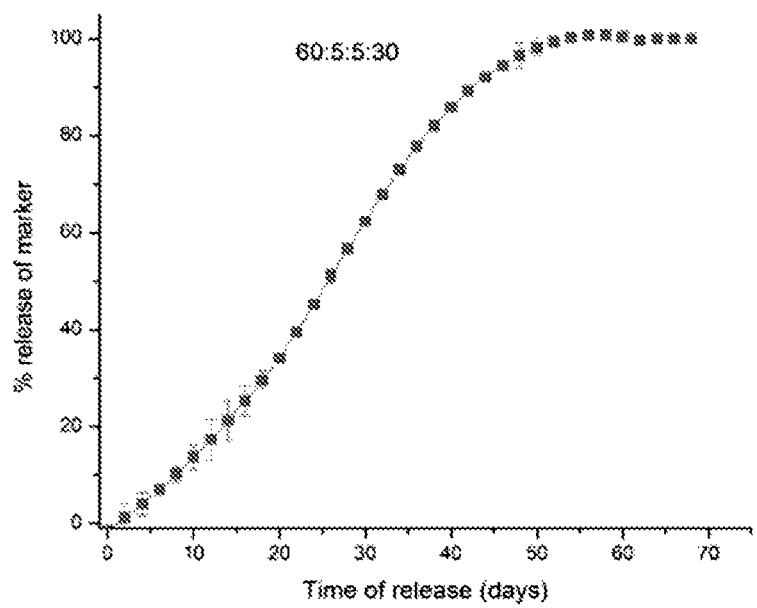

Formulation 1:
PC:PE:PG:Chol—60:10:0:30
Formulation 2:
PC:PE:PG:Chol—65:10:0:25
Formulation 3:
PC:PE:PG:Chol—60:5:5:30
Drug Release Studies (FIG. 23)
Formulation 1:
PC:PE:PG:Chol—60:10:0:30
Formulation 2:
PC:PE:PG:Chol—65:10:0:25
Formulation 3:
PC:PE:PG:Chol—60:5:5:30

7. Preparation of Lipisomes by Modified Method:

EPC, DPPE or PE-PEG 2000, DPPG and cholesterol were mixed at various molar ratios in a round bottom flask. To this, 10 ml of 2:1 ratio of methanol-chloroform mixture was added to make a uniform organic phase. The solvent was removed by rotovap to get a uniform film of lipid layer. This lipid layer was hydrated using the drug solution in 0.32 M mannitol to get a final phospholipid concentration of 10 mg/ml. The dispersion was sonicated for 5 min in a bath sonicator. The liposome solution was extruded around 10 times to obtain a uniform particle size of around 200 nm. Now, the solution was frozen at −70° C. for 30 min and then thawed to 40° C. for 20 min. The process was repeated at least 9-10 times and the final sample was lyophilized after removal of excess drug.

8. Preparation of Liposomes Containing Anti-Oxidants by Modified Method:

EPC, DPPE or PE-PEG 2000, DPPG and cholesterol were mixed at various molar ratios in a round bottom flask. To this, 10 ml of 2:1 ratio of methanol-chloroform mixture containing anti-oxidants like beta carotene or cantaxanthin were added to make a uniform organic phase. The solvent was removed by rotovap to get a uniform film of lipid layer. This lipid layer was hydrated using the drug solution in 0.32 M mannitol to get a final phospholipid concentration of 10 mg/ml. The dispersion was sonicated for 5 min in a bath sonicator. The liposome solution was extruded around 10 times to obtain a uniform particle size of around 200 nm. Now, the solution was frozen at −70° C. for 30 min and then thawed to 40° C. for 20 min. The process was repeated at least 9-10 times and the final sample was lyophilized after removal of excess drug.

9. Composition for Various Formulations:

| Formulation | PC | PE | PS | PE-PEG | PG | Chol | Other excipients |
|---|---|---|---|---|---|---|---|
| 1 | 70 | — | — | — | — | 30 | — |
| 2 | 69 | 8 | — | — | 8 | 15 | — |
| 3 | 65 | 5 | — | — | 5 | 25 | — |
| 4 | 60 | 5 | — | — | 5 | 30 | — |
| 5 | 60 | 10 | — | — | — | 30 | — |
| 6 | 60 | — | — | — | 10 | 30 | — |
| 7 | 55 | 10 | — | — | 10 | 30 | — |
| 8 | 50 | — | — | — | — | 50 | — |
| 9 | 40 | — | — | — | — | 60 | — |
| 10 | 46.7 | — | — | — | 20 | 33.3 | — |
| 11 | 33.4 | — | — | — | 33.3 | 33.3 | — |
| 12 | — | — | — | — | 66.7 | 33.3 | — |
| 13 | 46.7 | — | — | — | 20 | 33.3 | BC |
| 14 | 33.4 | — | — | — | 33.3 | 33.3 | BC |
| 15 | — | — | — | — | 66.7 | 33.3 | BC |
| 16 | 46.7 | — | — | — | 20 | 33.3 | CX |
| 17 | 33.4 | — | — | — | 33.3 | 33.3 | CX |
| 18 | — | — | — | — | 66.7 | 33.3 | CX |
| 19 | 80 | — | 20 | — | — | — | — |
| 20 | 70 | 10 | 20 | — | — | — | — |
| 21 | 60 | 20 | 20 | — | — | — | — |
| 22 | 50 | 30 | 20 | — | — | — | — |
| 23 | 40 | 40 | 20 | — | — | — | — |
| 24 | 69 | — | — | 8 | 8 | 15 | — |
| 25 | 65 | — | — | 5 | 5 | 25 | — |
| 26 | 60 | — | — | 5 | 5 | 30 | — |
| 27 | 60 | — | — | 10 | — | 30 | — |
| 28 | 55 | — | — | 10 | 10 | 30 | — |

B. Coating Fluorescein Encapsulated Liposomes on Intraocular Lenses

One of the goals of this study was to increase the lifetime of the liposomes in order to avoid multiple drug administration. The second goal is to treat endophthalmitis and inflammation that results from invasive ocular surgeries especially cataract surgery. In order to do this, artificial lenses can be coated with liposomes containing the drug.

Currently there are drug-eluting lenses available in the market, however these do not have a controlled drug release. The technology disclosed helps to control the dosage—the drug is incorporated in poly-lactic glycolic acid (PLGA) primary coating and also a secondary hydrophilic mucoadhesive coating matrix embedded with drug encapsulated liposomes. By using this method, the amount of drug that is administered is controlled and quantifiable.

A barrier that prevents the coating of the lenses is that they are composed of silicones that prevent hydrophilic solutions from adhering. In order to modify the hydrophobicity and allow for the liposome coating, oxygen plasma treatment was used. In this method, the surface of the lenses is temporarily modified by turning the silicon dioxide into silanol groups. The hydrophilic surface of the lens however is transient and lasts approximately 15-20 minutes. During this time, a primary coating of PLGA containing the drug is coated on to the lens using spin coating. PLGA is a hydrophilic polymer that is biodegradable and FDA approved. Different coatings containing PEG as a plasticizer and PLGA were used. The most efficient one was determined by using fluorescein in the PLGA and PEG coating solutions and visualizing the fluorescence using confocal laser scanning microscopy (CLSM). The most uniform coating was found to be the PLGA solution with 1% PEG. The imaging of all the coatings can be observed below.

Figure 24:
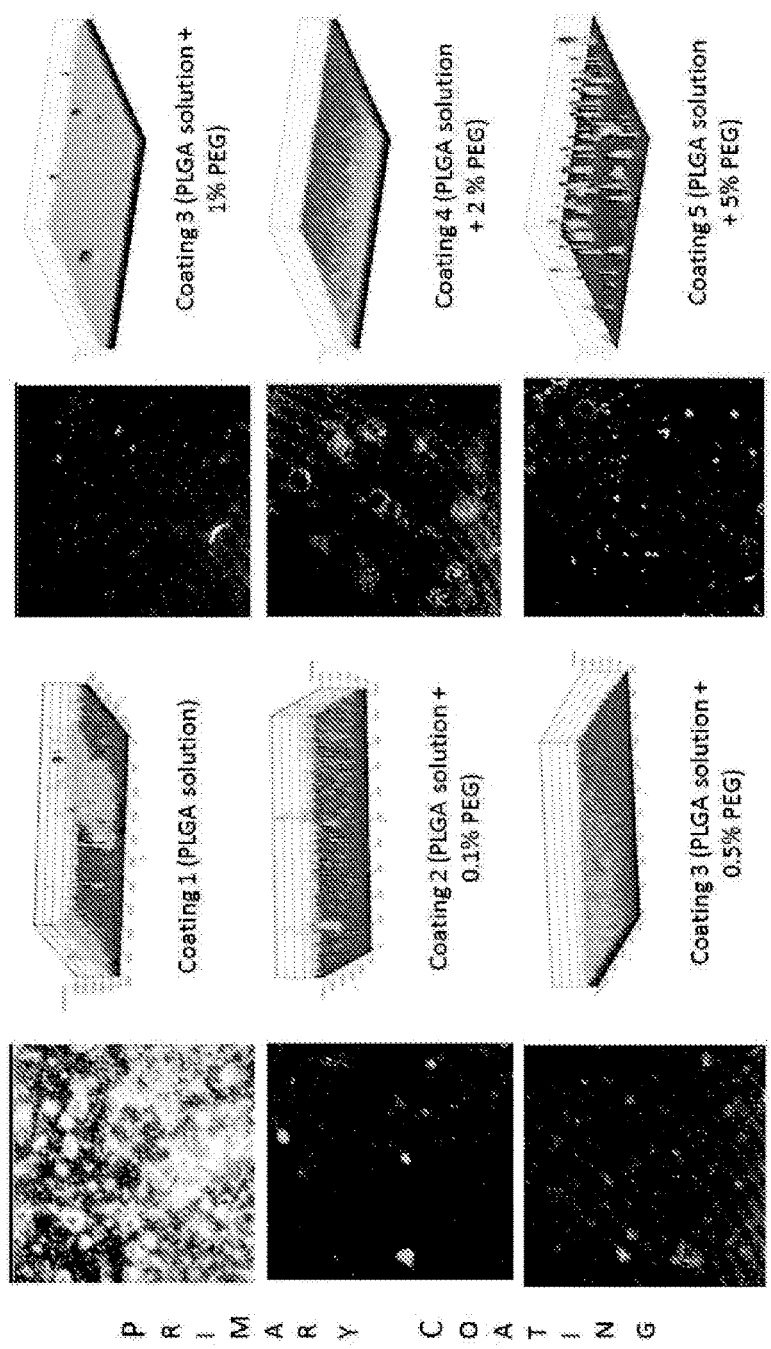
FIG. 24 shows fluorescent encapsulated liposomes on intraocular lenses; primary PLGA coating.

(a) Primary PLGA Coating (FIG. 24)

Using this formulation, a secondary coating was applied again by spin coating. In order to find the most suitable coating three polymers were tested, which included methyl cellulose, hydroxyl propyl cellulose, and hyaluronic acid. To these solutions, rhodamine was added and the fluorescence intensity measurement using a dual scanning system was used to construct the topography on the lens based on the intensities. The imaging of the secondary coatings appear in (FIG. 24) and reveals that hyaluronic acid and hydroxyl propyl cellulose gave the best results.

Figure 25:
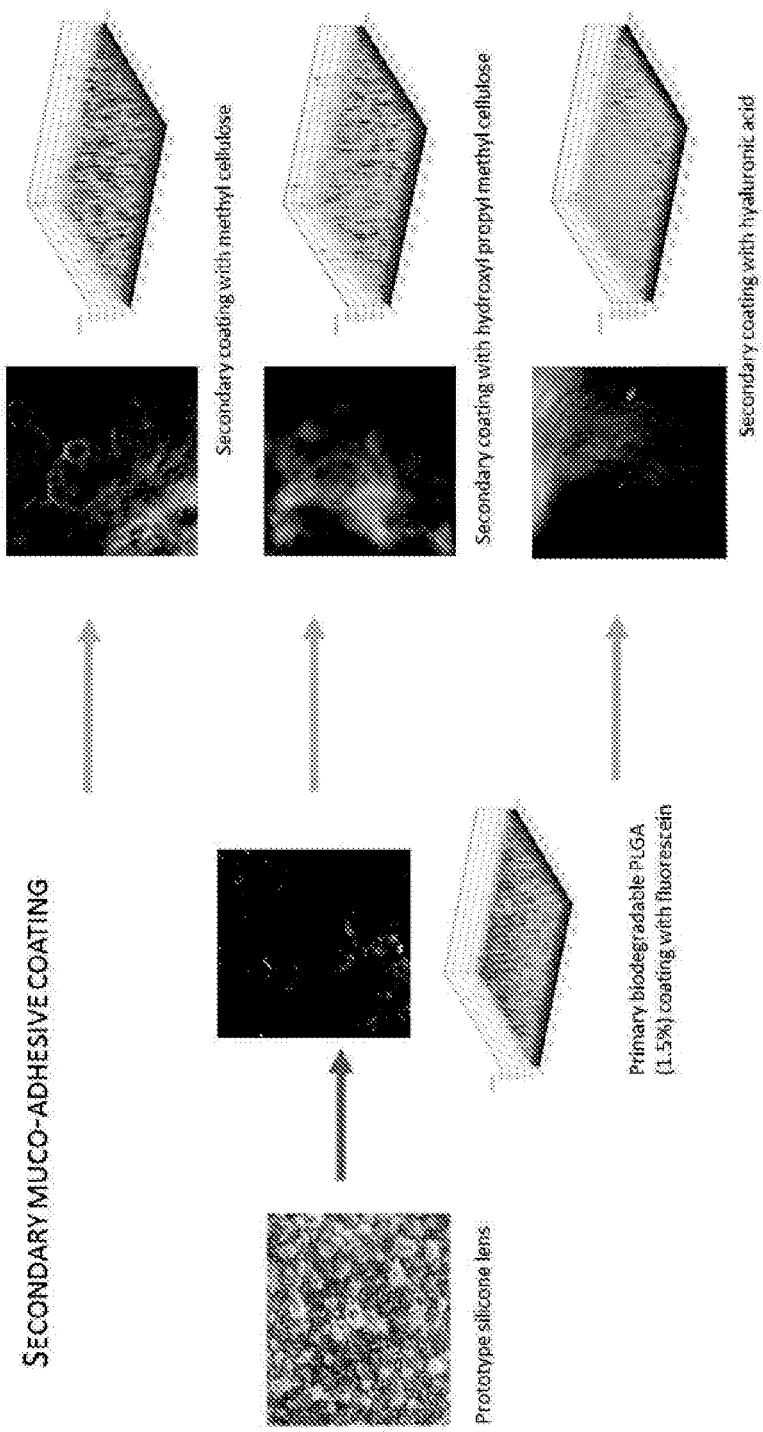
FIG. 25 shows fluorescent encapsulated liposomes on intraocular lenses; secondary hydrophilic mucoadhesive coating.

(b) Secondary Hydrophilic Mucoadhesive Coating (FIG. 25)

C. Fluorescent Tagged Human Serum Albumin as a Model for Macromolecules

In order to synthesize liposomes, different methods can be used. The method used herein for the encapsulation of fluorescein tagged human serum albumin was a combination of lipid hydration, extrusion and mannitol freeze thaw methods. The human serum albumin was used as a protein model that is close in molecular weight to Lucentis®.

When synthesizing liposomes using the modified method, the phospholipids are first dissolved using organic solvents such chloroform and methanol mixtures. In general the solutions are prepared by mixing 10-20 mg of phospholipids per milliliter of organic solvent. The phospholipids and organic solvents are then thoroughly mixed. Then, the solvents are evaporated using a rotary evaporator. The temperature of the solution was kept above the transitory temperature where the liposomes undergo a phase change. The evaporation of the solvents leaves behind a thin lipid film that is rehydrated by adding an aqueous medium that contains the drug that is to be encapsulated. During the rehydration time, the phospholipids are vigorously shaken and left overnight in order to improve the homogeneity of the size. The particle size of the liposomes was then reduced by extrusion. Extrusion is a method where pore size filters are used. The liposomes solution is force to go through the filter by increasing the pressure. The process results in liposomes with a uniform smaller particle size. Then, the liposomes are put through 10 freeze thaw cycles to improve the encapsulation efficiency. The solution is then lyophilized, which yields a fluffy substance. The advantage of using mannitol/trehalose in the procedure is that the encapsulation of the drug is increased. The efficiency of encapsulation can be increased by 20% as the number of freeze-thaw cycles increase. The modified method gave best results in terms of particle size as well as encapsulation. The size of the liposomes was then measured using dynamic light scattering as shown in the figure below. The TEM images of the formulations are displayed in FIG. 26(A)(B).

Figure 26:
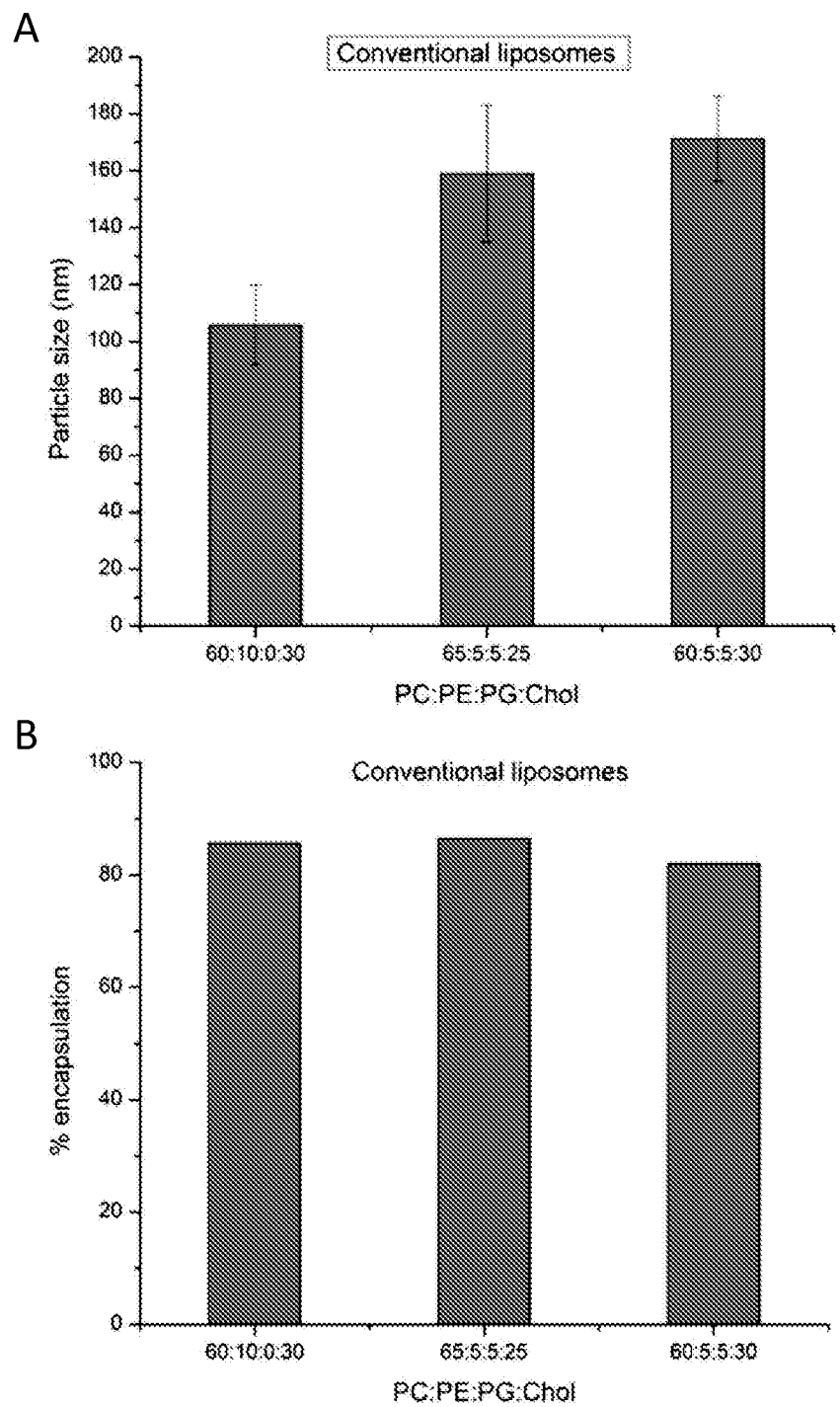
FIG. 26 shows results of fluorescent tagged human serum albumin as a model for macromolecules, conventional liposomes; (A) particle size distribution; (B) % encapsulation.
Figure 27A:
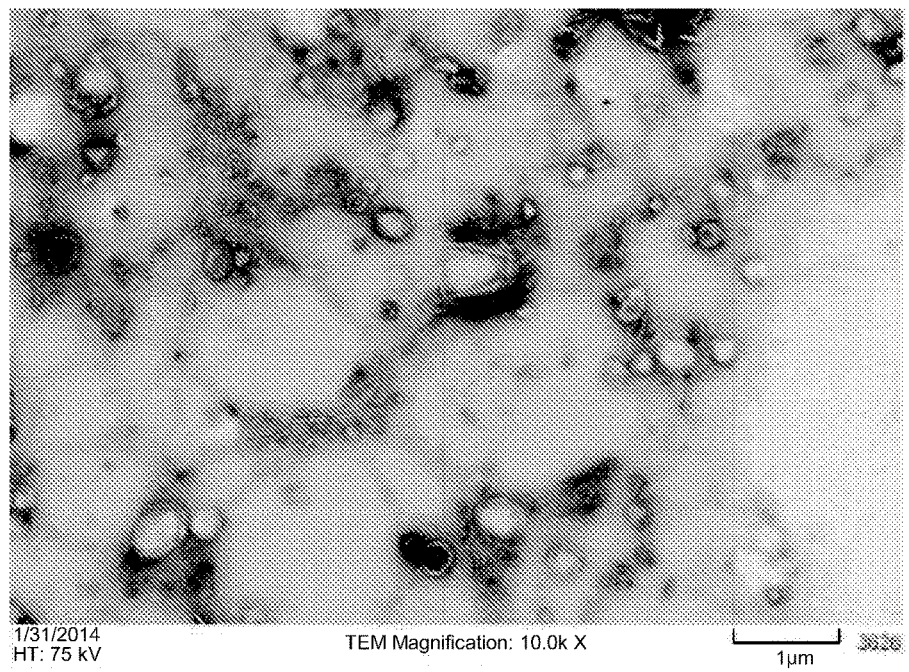
FIG. 27: shows TEM images (A) formulation 1(B) formulation 2 (C) formulation 3.
Figure 27B:
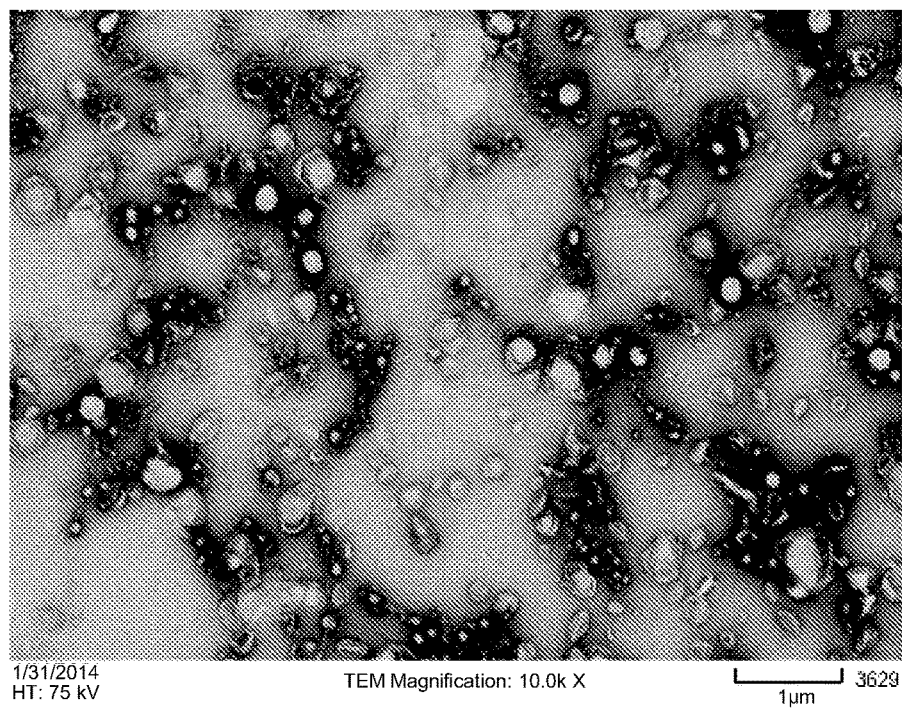
Figure 27C:
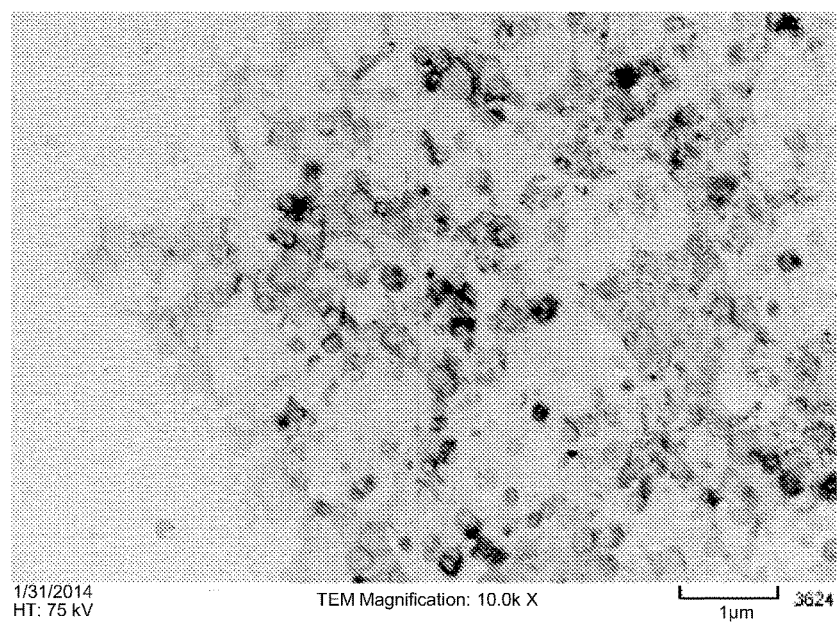

(a) Conventional Liposomes (FIG. 26 (A) Particle Size; FIG. 26(B) % Encapsulation)

FIG. 27, A, B, C

Formulation 1:

PC:PE:PG:Chol—

60:10:0:30

Formulation 2:

PC:PE:PG:Chol—

65:10:0:25

Formulation 3:

PC:PE:PG:Chol—

60:5:5:30

Figure 28:
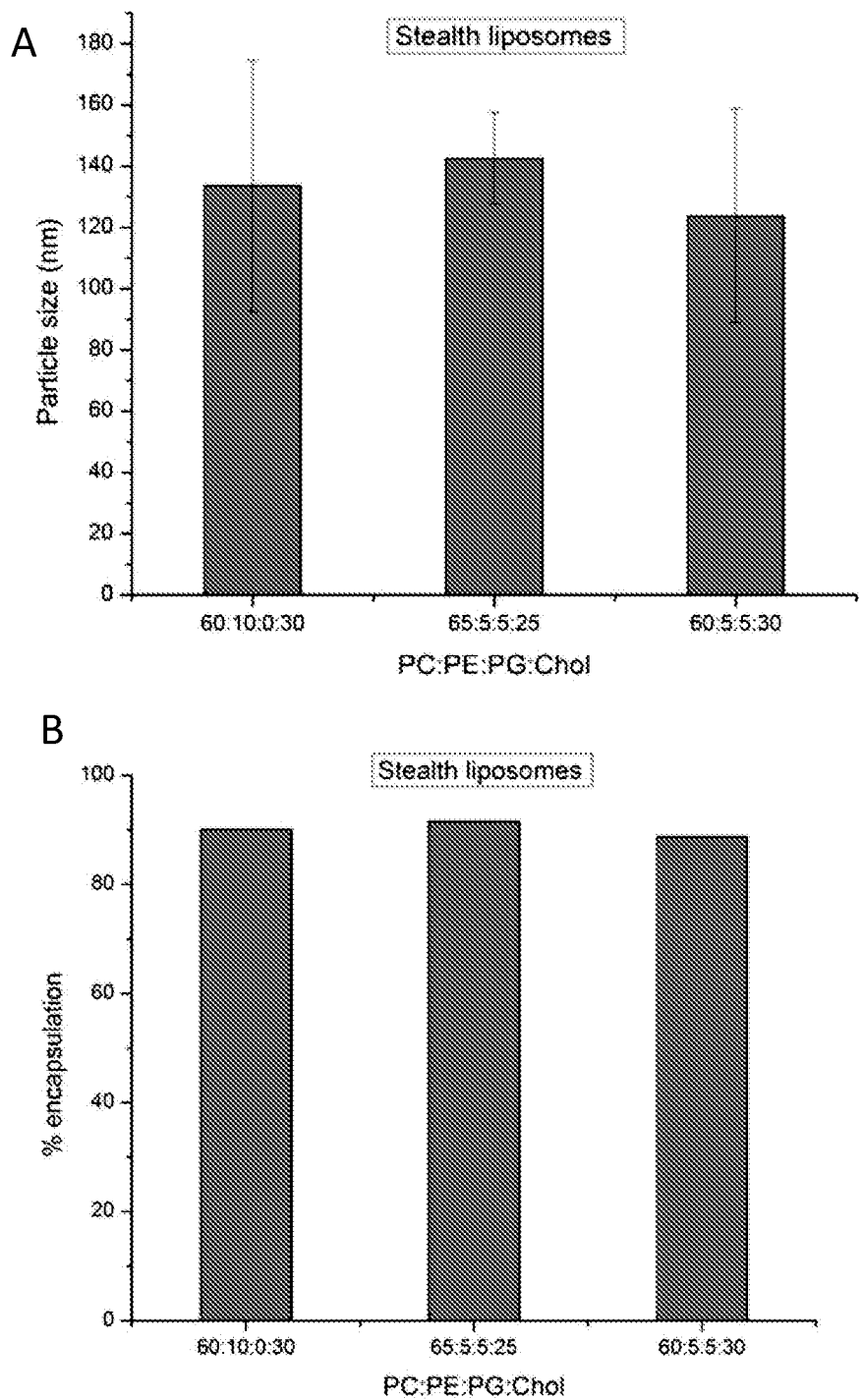
FIG. 28 shows results of stealth liposomes (A) particle size distribution; (B) % encapsulation.
Figure 29A:
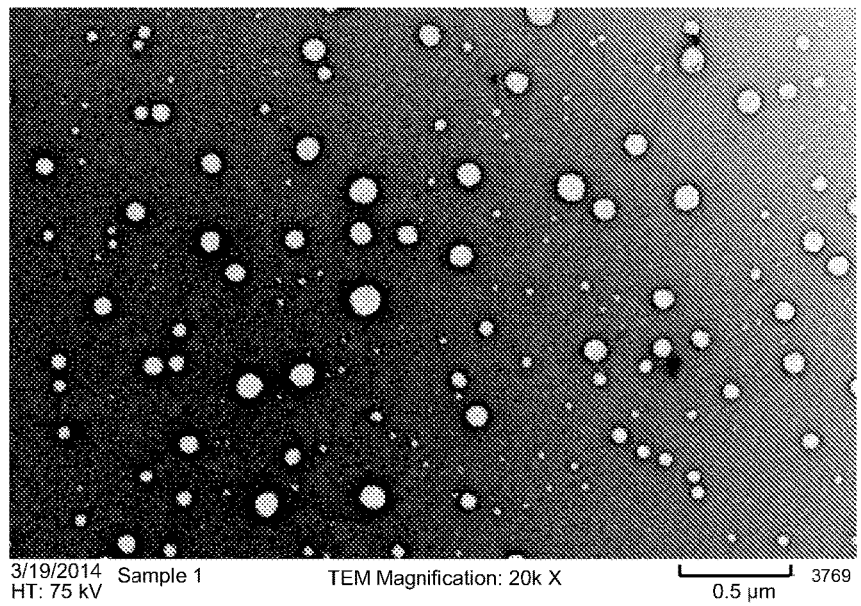
FIG. 29: shows TEM images (A) formulation 1; (B) formulation 2; (C) formulation 3.
Figure 29B:
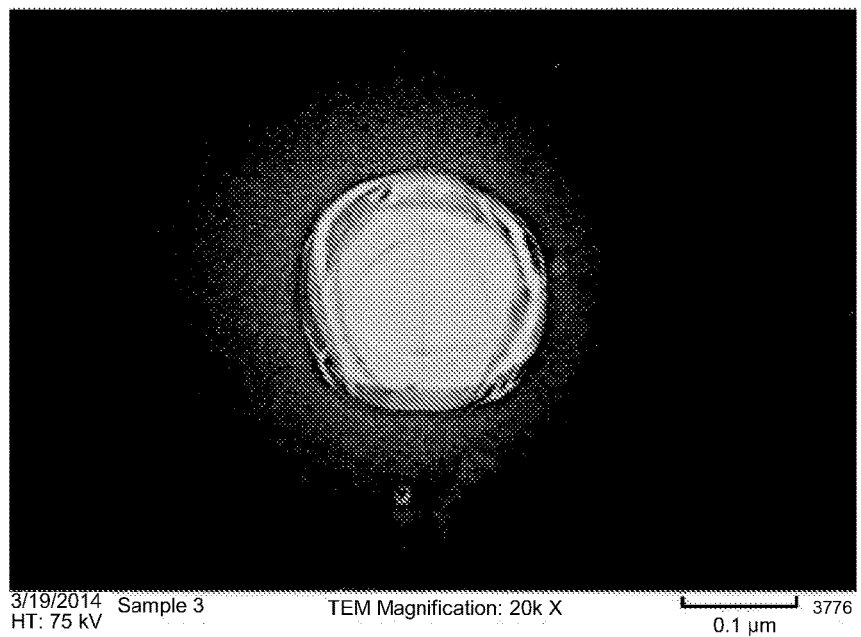
Figure 29C:
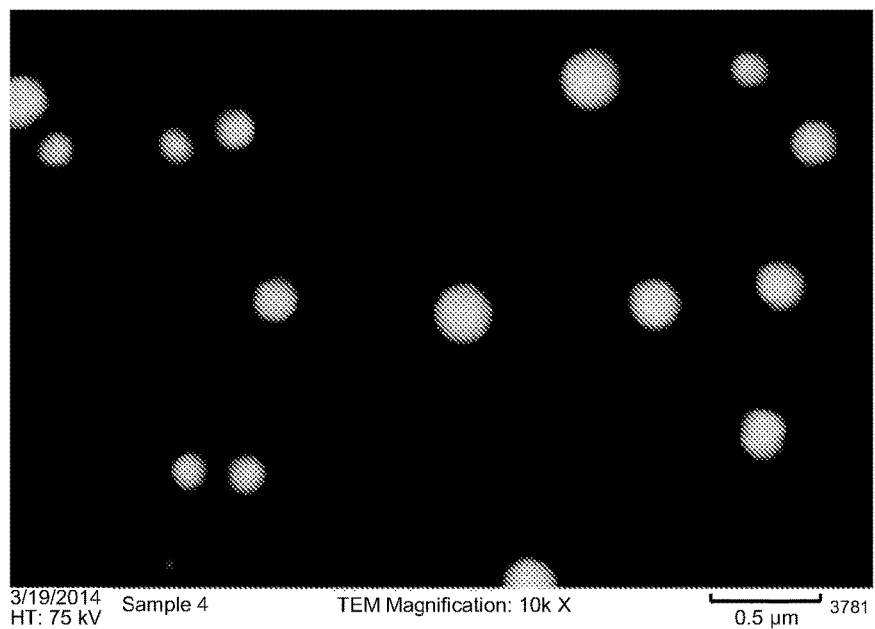

(b) Stealth Liposomes or PEGylated Liposomes (FIG. 28, A, B)

Conventional liposomes are liposomes that do not contain any surface modifications. Although the liposomes protect the encapsulated molecule from degradation, when administered into the body they are easily captured by the mononuclear phagocyte system and are removed from the blood stream. The elimination of conventional liposomes is a great disadvantage since their degradation prevents the drug from reaching its target zone in the back of the eye. The removal of the liposomes from circulation first begins when opsonin serum proteins attach to the surface. These proteins mark the liposomes for degradation and allow the binding phagocytic cells to the liposomes.

In order to increase the circulation longevity of liposomes, surface modification by hydrophilic polymers can be employed. PEG is a hydrophilic polymer that is biocompatible and biodegradable. When a liposome surface is modified by PEG, the polymer provides a hydrophilic protective layer that is able to repel the adsorption of proteins, such as opsonin, through steric repulsion forces.

The size of the liposomes was then measured using dynamic light scattering as shown in the figure below. The encapsulation efficiency was determined based on the fluorescence of the tag on the protein. TEM images of the formulations are also displayed below. The drug release studies were performed using the SOTAX USP 4 dissolution apparatus.

FIG. 29, A, B, C

Formulation 1:

PC:PE:PG:Chol—60:10:0:30

Formulation 2:
PC:PE:PG:Chol—65:10:0:25
Formulation 3:
PC:PE:PG:Chol—60:5:5:30
(c) Drug Release Studies

TABLE 1

Conventional Liposomes

| Composition PC:PE:PG:Chol | Time for 100% release (days) |
|---|---|
| 60:10:0:30 | 81 |
| 65:5:5:25 | 102 |
| 60:5:5:30 | 111 |

TABLE 2

Stealth Liposomes

| Composition PC:PE-PEG2000:PG:Chol | % Release in 50 days | Estimated time for 100% release (days) |
|---|---|---|
| 65:5:5:25 | 20.4 | 240 |
| 60:10:0:30 | 28.4 | 173 |
| 60:5:5:30 | 21.2 | 231 |

From the results that were obtained, it can be observed that PEGylation increased the time of drug release. The slower time release of drugs that are encapsulated using stealth liposomes validates that liposomes can be used as slow drug delivery systems. The slow release of the drug using liposomes thus can decrease the frequency of injections and the cost for the treatment of AMD and DR.

D. Radial Electron Density Profiles of the Liposomes was Used to Study the Molecular Level Interactions and Also to Determine the Exact Location of the Drug Embedded in the Liposomes The purpose of this analysis was to optimize compositions of liposomal formulations to be used as drug delivery vehicles. Liposomes are versatile and can be used to encapsulate various ocular drugs ranging from small drugs to macromolecules like proteins. Some of the ocular drugs currently available in the market include Bevacizumab (Avastin), Ranibizumab (Lucentis), Gentamicin, Bacitracin, Polymyxin B, Gramicidin, Prednisolone, Dexamethasone, Neomycin, Flurbiprofen sodium, Chloramphenicol, Timolol, Ciloxan, Miconazole, Tobramycin and Triamcinolone.

The molecular level design of liposomes to carry protein drugs to treat ocular disease is useful to design liposomal formulations with varying degrees of lamellarity and size so as to obtain sustained release of the drugs. In addition, liposomes designed with PEG surface modification will minimize the toxicity of the drugs as well as increase the longevity of the liposomes.

In addition, looking at very small angle scattering, the interactions between different vesicles, should provide guidance to improve the stability of prepared suspensions. A number of parameters including the lipid composition, the liposome size, presence of adjuvants like anti-oxidants, cryo-protectants and the type of drug encapsulated are varied.

Selective labeling of lipids and drugs with heavy elements such as Bromine may increase the sensitivity of the x-rays to obtain more refined structural details. Consequently examination of a single lipid-drug system provide SAXS patterns between neat liposomes, liposomes with drug encapsulations and stealth liposomes (PEGylated liposomes). Brominated drugs may enhance feature contrast in the SAXS patterns, and the tolerance of the samples to X-ray damage.

(a) Particle Size Determination

SAXS experiments were conducted using different liposomal formulations—conventional liposomes, conventional liposomes with anti-oxidant Vitamin F and liposomes with a cryoprotectant. The particle size was measured using Dynamic Light Scattering as shown in Table 3.

TABLE 3

| Formulation | Particle size range (nm) |
|---|---|
| 1) Conventional liposomes | 173.2-200.3 |
| 2) Conventional liposomes with anti-oxidant Vitamin F | 170.3-245.9 |
| 3) Liposomes with a cryoprotectant | 211.4-244.5 |

Figure 30:
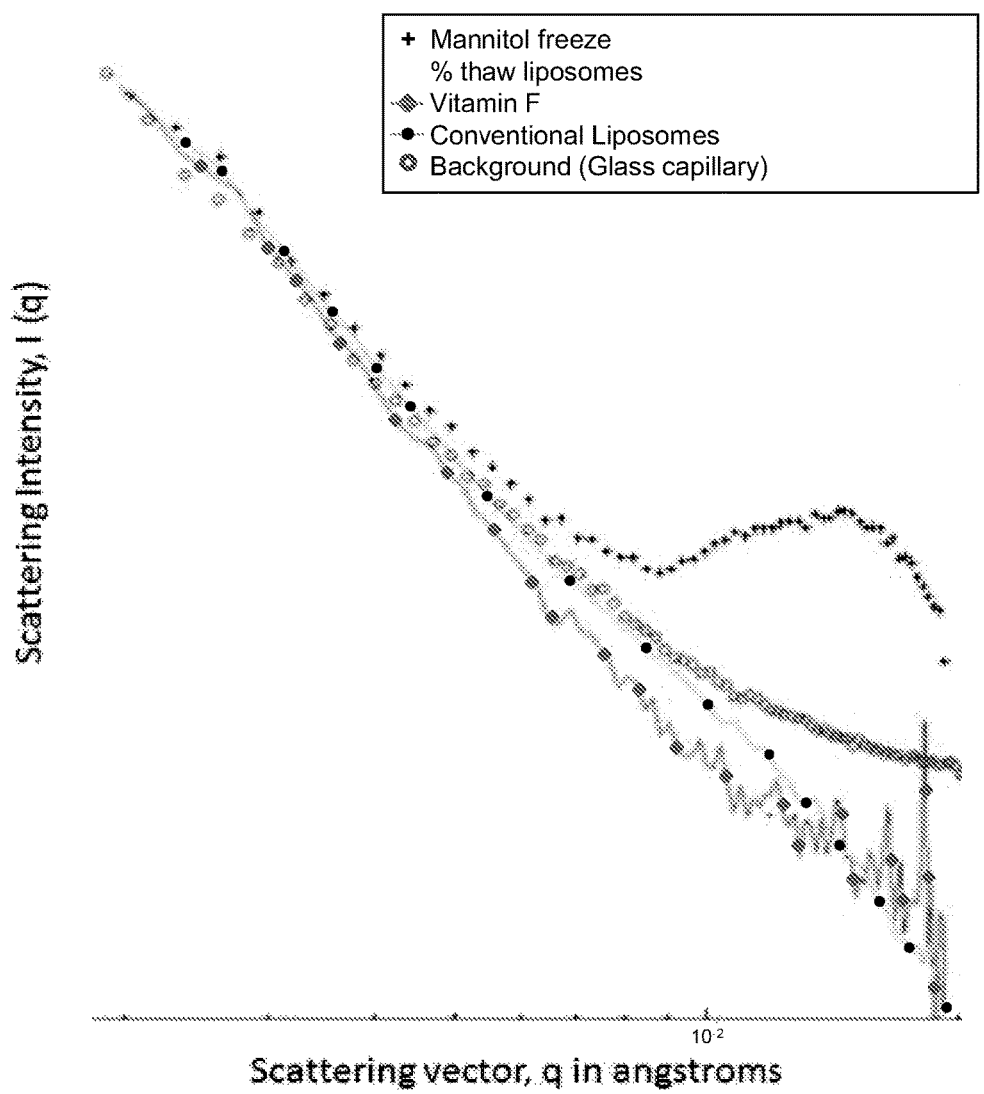
FIG. 30 is an SAXS profile for various formulations at very low angles +=mannitol freeze % thaw liposomes; ◆=Vitamin F; ▬=Conventional Lipisomes; ○=Background (Glass capillary).

(b) SAXS Profile for Various Formulations at Very Low Angles (FIG. 30)

The scattered intensity curve features two regimes corresponding to two different length scales. In the case of low polydispersity unilamellar vesicles (ULVs), high frequency oscillations are observed at length scales corresponding to $q<0.03$ A°. These oscillations originate from scattering taking place over the entire vesicle and are inversely proportional to the ULV's radius, R. However, this feature decays quickly with increasing q. Scattering information from $q>0.03$ A° is mostly attributed to the bilayer itself. For these experiments, the scattering intensities were measured between 0.002-0.02 A° and the scattering profiles in this region can be seen as follows. From the data obtained, scattering from cryoprotectant freeze dried liposomes appears to be due to interaction of mannitol with the lipid bilayers and also the diffusion of mannitol between the layers helping in creating an osmotic balance.

Figure 31:
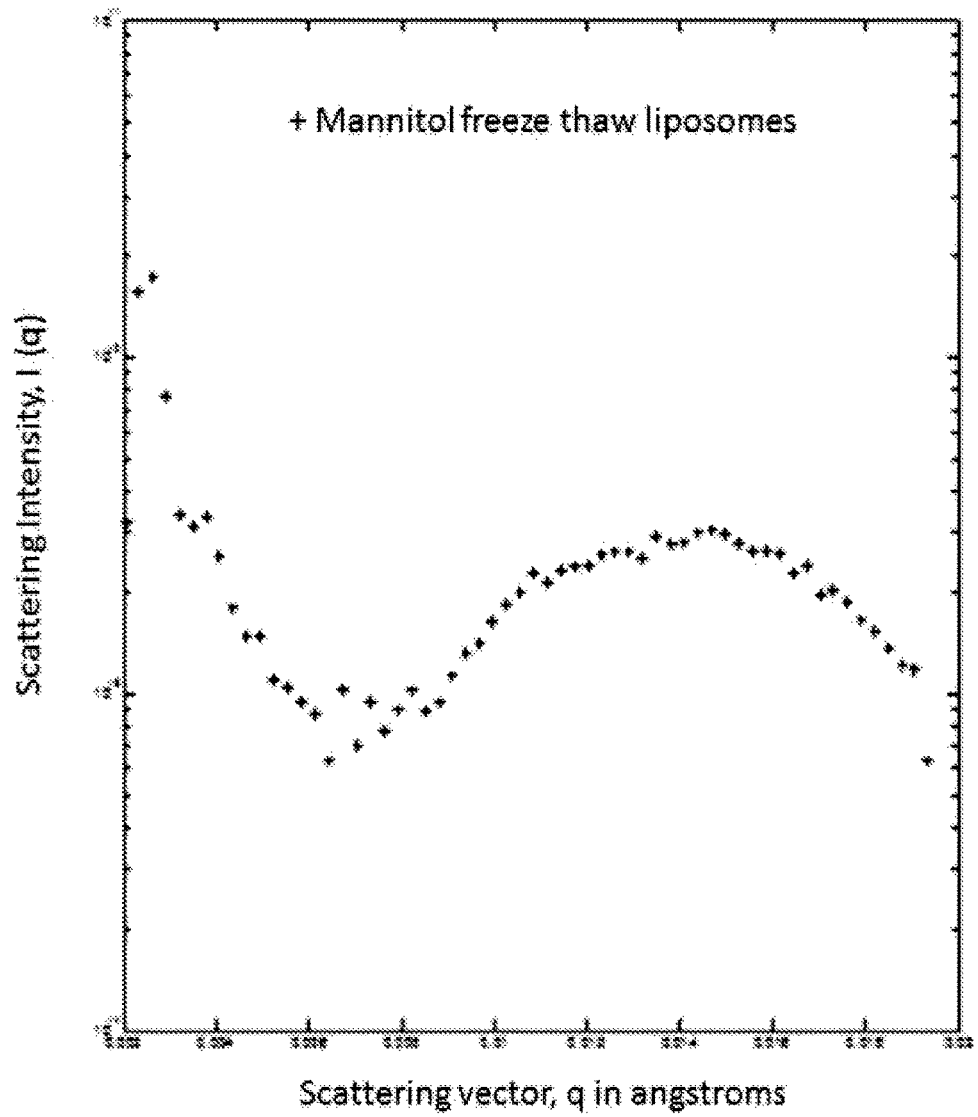
FIG. 31 is a scattering profile for cryoprotectant mannitol freeze-dried liposomes.

(c) Scattering Profile for Cryoprotectant (Mannitol) Freeze Dried Liposomes (FIG. 31)

The scattering intensities between 0.002-0.02 A° were measured and the scattering profiles in this region can be seen as above. From the data obtained, it appears that the scattering from cryoprotectant freeze dried liposomes might be due to interaction of mannitol with the lipid bilayers and also the diffusion of mannitol between the layers helping in creating an osmotic balance.

E. Separation of Free Drug

Free unentrapped drug was separated from the liposomes by centrifugation at 17000 rpm for 1 hr at 4° C. The pellets formed were washed with distilled water twice and then re-suspended, centrifuged again for 1 hr.

F. Encapsulation Efficiency

The change in fluorescence signal can be used to assess the membrane permeability. Interactions of certain solutes such as some drugs or antimicrobial peptides could reduce the stability and/or change the permeability of the bilayer membrane. The extent of the leakage from an encapsulated liposome due to contact with a certain solute is determined from the relative fluorescence (% F) of the leaked marker and is calculated by equation—

$$F = \left[\frac{F_t - F_0}{F_\infty - F_0}\right] \times 100\%$$

Where, $F_t$—Fluorescence of liposomes after incubation with solute $F_0$—Initial fluorescence due to dilution in an isomolar buffer $F_\infty$—Maximal fluorescence after lysis by Triton X-100

G. Particle Size Determination of Liposomes Using Dynamic Light Scattering (DLS)

The particle size was measured by Dynamic light scattering (DLS) on a Brookhaven BI-200SM Research Goniometer and Laser Light Scattering System (5 mW He—Ne laser, λ=632 nm) using CONTIN software. Cumulant analysis was used to obtain the particle size distribution from the correlograms generated by the software. The temperature was fixed at 25° C. This random motion is modeled by the Stokes-Einstein equation. Below the equation is given in the form most often used for particle size analysis.

$$D_h = \frac{k_B T}{3\pi\eta D_t}$$

Where, $D_h$ is the hydrodynamic diameter
$D_t$ is the translational diffusion coefficient
$k_B$ is Boltzmann's constant
T is thermodynamic temperature
η is dynamic viscosity H. Characterization of Liposomes Using Negative Staining Transmission Electron Microscopy Briefly, a drop of a water-diluted suspension of the liposomes (about 0.05 mg/mL) was placed on a 200-mesh formvar copper grid, allowed to adsorb and the surplus was removed by filter paper. A drop of 2% (w/v) aqueous solution of uranyl acetate was added and left in contact with the sample for 5 minutes. The surplus water was removed and the sample was dried at room conditions before the vesicles were imaged with a TEM operating at an acceleration voltage of 200 KV I. Drug Release Studies Using Liposome Solutions Drug release studies were performed using USP 4 dissolution apparatus (SOTAX Corporation). The flow rate was maintained at 0.5 ml/min. Aliquots were removed at regular intervals and the concentration of the drug released was measured using fluorescence spectrophotometry.

J. Coating Liposomes on the Surface of IOLs

The primary coating solution was prepared by mixing appropriate pre-evaluated amounts of PLGA in volatile solvent. The PLGA solution is spin coated at 4000 rpm on plasma treated intraocular lenses. The lyophilized liposomes were mixed into a hydrophilic coating material and coated on the top of PLGA smeared IOLs and vacuum dried for 24 hr. The final products are stored in a sealed container and stored appropriately till further use. Using the primary coated lenses, a secondary coating was applied again by spin coating. In order to find the most suitable coating three polymers were tested, which included methyl cellulose, hydroxyl propyl cellulose, and hyaluronic acid. To these solutions, rhodamine was added and the fluorescence intensity measurement using a dual scanning system was used to construct the topography on the lens based on the intensities.

K. Characterization of Coatings Using Confocal Laser Scanning Microscopy

CLSM analysis was performed with a Zeiss LSM 5 Pascal Confocal Laser Scanning Microscope equipped with Argon (458, 488, and 514 nm) and HeNe (543 nm) lasers. In order to characterize and select the ideal composition for the coatings, Rhodamine was mixed with the PLGA coating and fluorescein encapsulated liposomes in hydrophilic coating material were used for secondary coating.

L. Drug Release Studies Using Liposome Solutions and Coated IOLs

Drug release studies were performed using USP 4 dissolution apparatus (SOTAX Corporation). The coated IOLs were placed in the flow cells such that the buffer would wash the coating as well as the liposomes from the surface of the lenses over a period of time. The flow rate was maintained at 0.5 ml/min. Aliquots were removed at regular intervals and the concentration of the drug released was measured using fluorescence spectrophotometry.

M. Lipid Mixture

The lipid mixture was made using 100 mg of egg phosphatidyl choline (PC), 40 mg of cholesterol and 10 mg of phosphatidyl glycerol (PG), in 5 ml of chloroform/methanol solvent mixture (2:1 vol./vol). The lipid solution was introduced into a 250 ml round bottom flask with a ground glass neck. The flask was attached to a rotary evaporator. The liquid was evaporated from the solution, and a dry lipid film was deposited on the walls of the flask. Then, 5 ml of drug solution was added to the film and mixed vigorously for 30 min. The suspension, so formed, was left for 24 hours for the liposomes to swell. In order to get unilamellar liposomes, the solution was sonicated for 1 hour. The particle size was measured using Dynamic Light Scattering®.

N. Drugs

A series of encapsulated drugs are described that are suitable to coat IOLs, contact lenses and ocular stents. The drugs are encapsulated in liposomes which are in turn embedded in a polymer coating that is then applied to a contact lens, intraocular lens or an ocular stent. The embedded drugs are useful to treat various maladies such as dry eye or infection after cataract surgery, including treatment with an antibiotic or with prednisolone to fight post-operative inflammation. Other embedded drugs include antibiotics such as gatifloxicin, anti-inflammatories such as dexamethasone, prednisolone and other steroids.

Anti-vascular endothelial growth factor (Anti-VEGF) drugs and antioxidants are also used to treat age-related macular degeneration (AMD) and related conditions. The value of these nanodrugs is that they result in a slow release of the drug, increasing its residence time. For example, antioxidants are a class of drugs that are the phosphorylated thiols. The thiol is released in a cell via the hydrolysis of the phosphate by alkaline phosphatase, which can then control oxidative destructive processes.

O. Detection of Drug Release

One aspect of the methods disclosed herein is the detection of drugs following the release of highly fluorescent materials, such as fluorescein, from the coated IOL, which is placed in a cuvette. The stability of each coating, the concentration of the released compound, and the time it takes to release the compound, are determined. All of these parameters are necessary to determine the feasibility of the use of each emulsion in the human eye. In order to extrapolate to human use, animal experiments are performed in conjunction with an ophthalmologist. First, fluorescence is detected throughout the eye. However, because most drugs are not fluorescent, other methods are also suitable.

1. Fluorescence

Fluorescein was used as an encapsulated compound (substance) in each of the emulsions tested because its release can be readily detected. A fluorotron detects fluorescein directly, for example, in a rabbit model. From these studies the release of drugs are timed and estimates are made of the final concentrations released.

Figure 2:
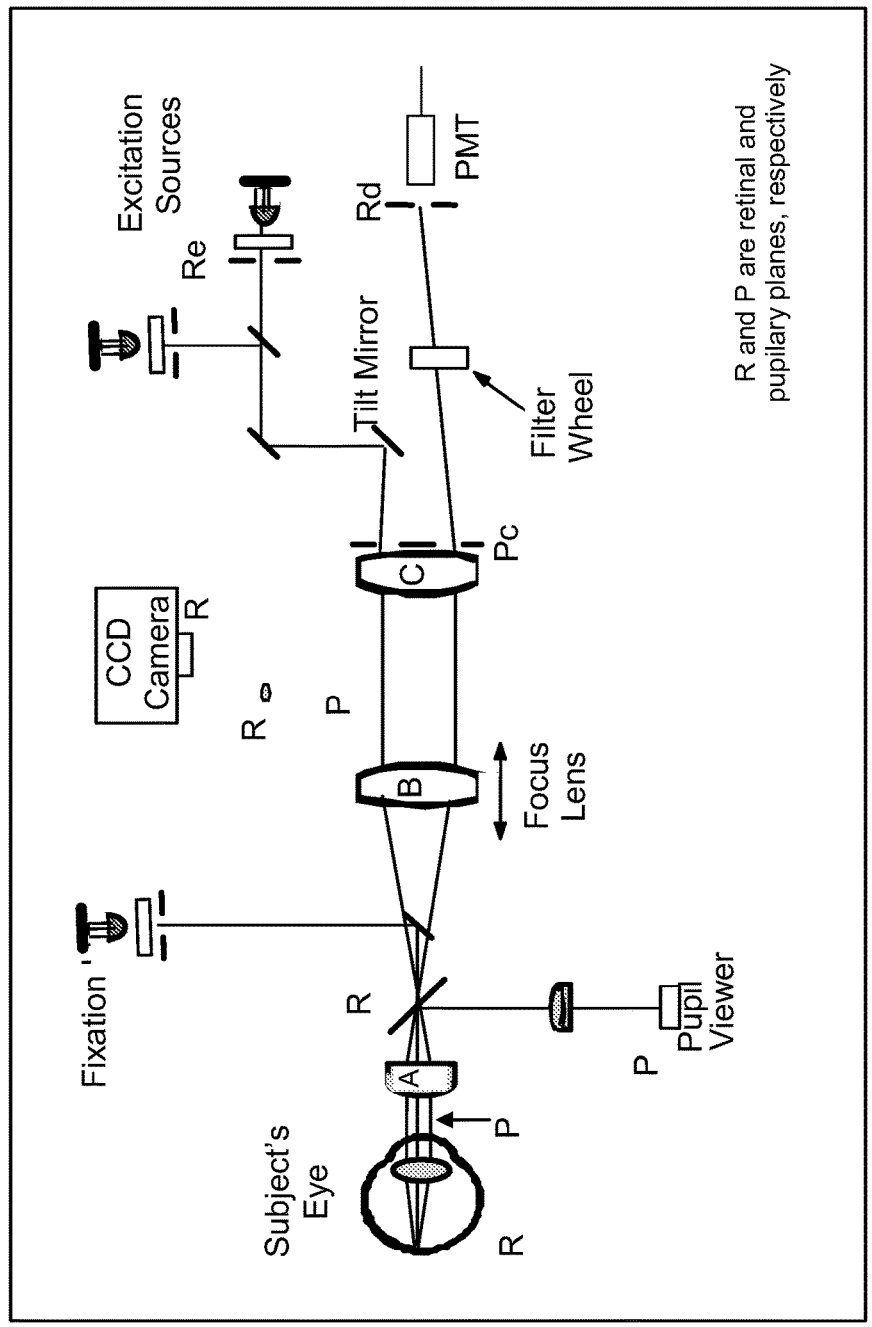
FIG. 2 is a diagrammatic representation of an optical layout of a fluorescent system.
Figure 3:
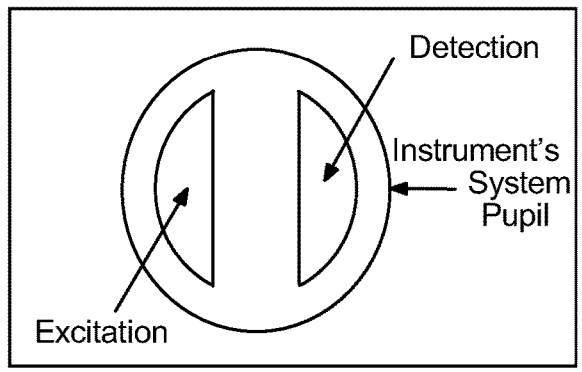
FIG. 3 is a diagrammatic representation of the configuration of the pupils of the system in FIG. 2, in the plane of the subject's pupil.

The optical components of a Fluorotron are a platform for a prototype. FIG. 2 shows the main optical layout and components of the system. The excitation source irradiates—through a bandpass filter—an aperture Re which is imaged by the optical system on the retina as a 1.9×0.10 mm slit in the eye. Light reemitted (reflection and fluorescence) by the fluorescent probe is sampled from the 1.9×0.10 mm slit, aligned to the excitation and defined by an aperture Rd (which is confocal to Re). Lens B is used to scan Rd and Re along the optical axis. The excitation and detection pupils are defined by the apertures Pc, located very close to lens C. These pupils are imaged anterior to the subject's cornea by the optics. The configuration of these pupils in the plane of the subject's pupil is shown (FIG. 3, left). This configuration minimizes contributions from the fluorescence outside of the measurement point by separating the excitation and detection paths. Another bandpass filter rejects reflected excitation light, and the fluorescence collected by aperture Rd is detected using a red-extended end-on photomultiplier tube selected for low (<100 count/sec.) dark noise (Hamamatsu Photonics K.K., Model R1463P-SELECT).

Figure 4:
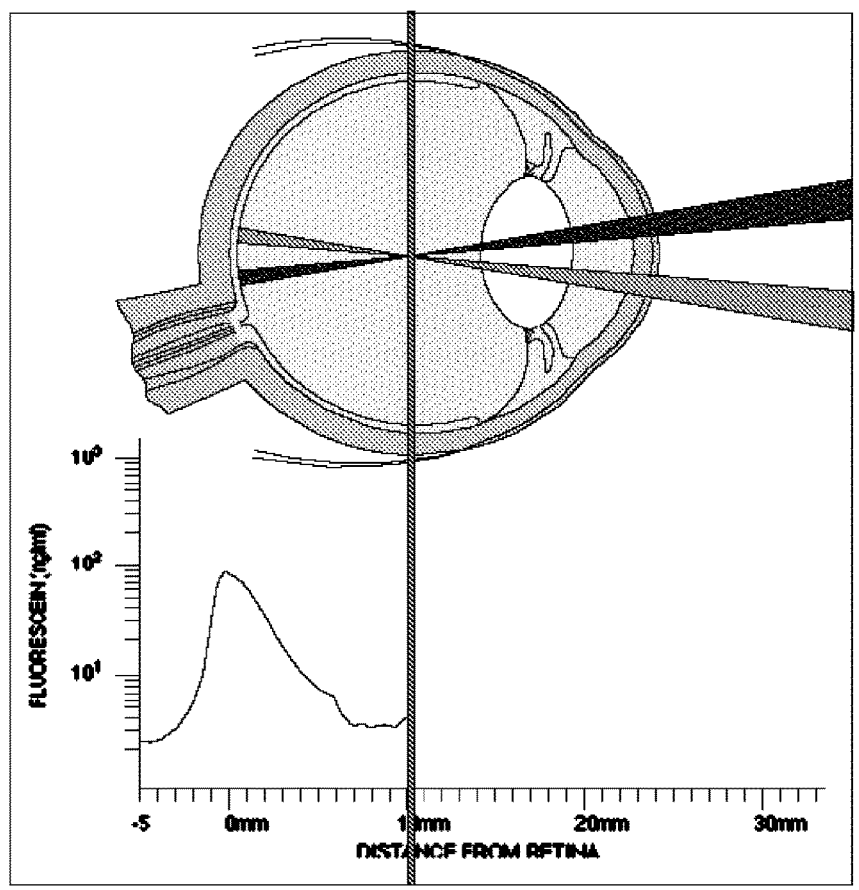
FIG. 4 shows a typical output from the fluorotron in a steady state experiment, an optical system for achieving high axial separation.

FIG. 4 gives a typical output from the Fluorotron in a steady state experiment. As the focus lens is driven forward the emission signal is continuously monitored from retina to cornea, giving an intensity output. For pulsed fluorescence studies, the excitation bandpass filter is fixed at 400 nm and a longpass filter that is matched to the fluorescence emission maximum is placed in front of the photomultiplier tube detector.

The steady state experiment is more sensitive than the pulsed method, is monitored continuously and readily scanned from the back of the eye to the front. But the intensity of the fluorescence is determined in part by the concentration of fluorophore. This can be circumvented by determining the concentration of the probe. The pulsed method takes more time, but the lifetime is invariant with concentration which is ascertained directly from the measurements. These methods are therefore complimentary.

2. Direct Detection

There are two types of strategies for ocular drug delivery. Relatively short term treatments as would be needed for infections after surgery, or long term treatments with drugs that slow the growth of new blood vessels. (This is a major complication of diseases such as age-related macular degeneration and diabetic and myopic retinopathy.) In each case, vehicles such as liposomes and emulsions that are either suspensions or embedded in coatings that are applied to prosthetic devices, are used and the drug(s) are slowly released over time. As examples, the solutions can be directly injected into the vitreous and the coatings can be used on intraocular lens (IOL) implants that are inserted during cataract surgery. In each case, it is essential to determine how long the drug will be released and what concentration it will attain. Fluorescein, a fluorescent dye, is encapsulated in the vehicles (vesicles e.g. liposomes) and while encapsulated, no fluorescence is observed. As the fluorescein is slowly released out into the solution, an increase in fluorescence intensity is observed. This serves to compare various nanoparticle formulations, but does not give insight into the treatment using real drugs such as coatings with antibiotics for prevention of post-operative endophthalmitis or with prednisone, dexamethasone or other steroid drugs for prevention of post-operative inflammation. Further, the fluorescence assay does not give any information on the changes in drug concentration as a function of time.

Figure 5:
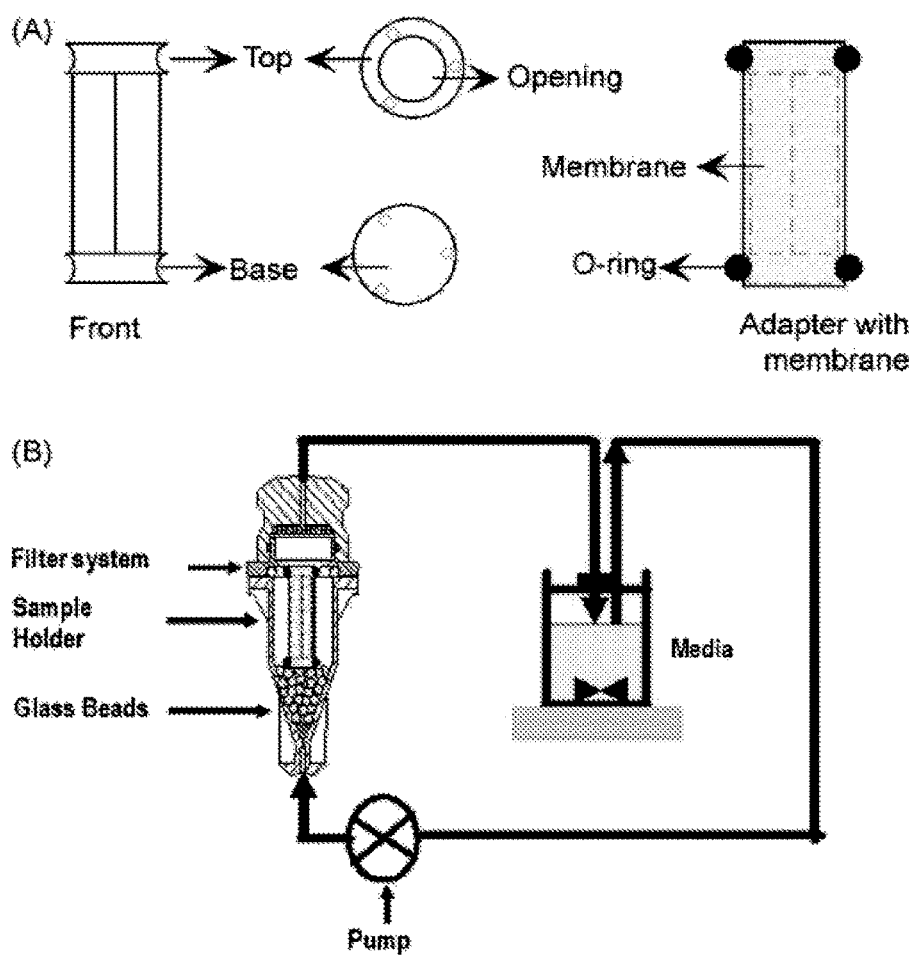
FIG. 5 is a schematic of an apparatus to determine real drug concentrations, including an apparatus that collects aliquots of samples and concentrates the samples.

In order to determine real drug concentrations that are being released, an apparatus is needed such as the SOTAX® flow-through cell systems (FIG. 5) which automatically collects aliquots and concentrates the samples.

Figure 6:
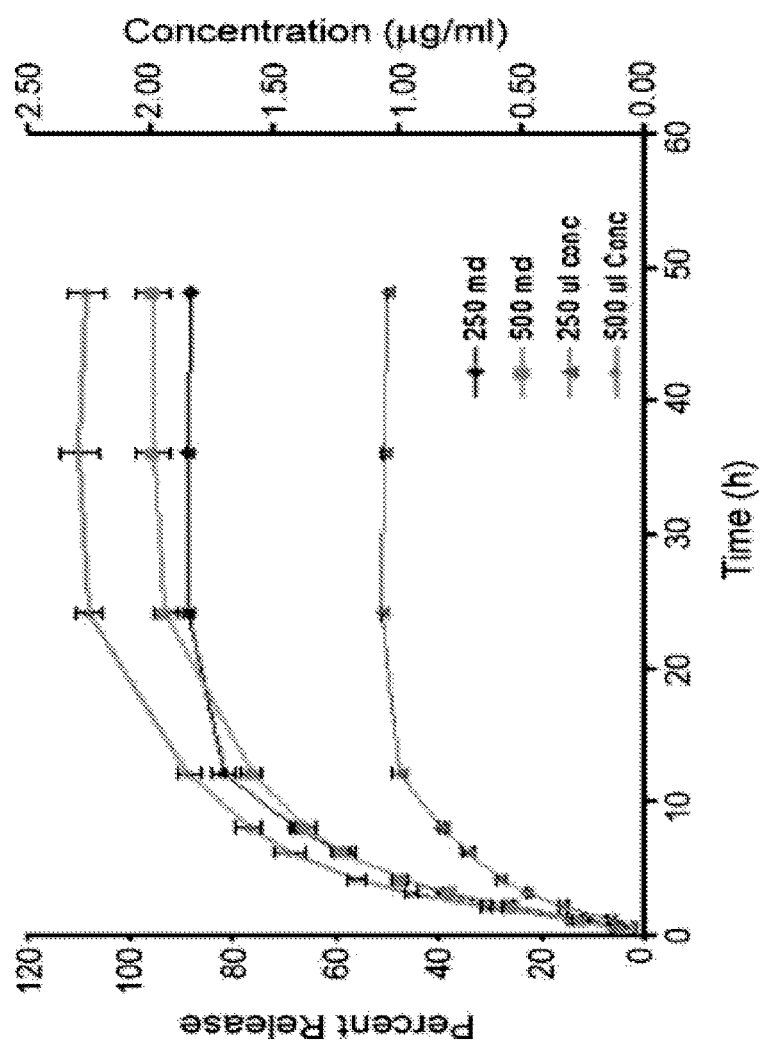
FIG. 6 is a graph illustrating concentration of a drug over time.
Figure 7:
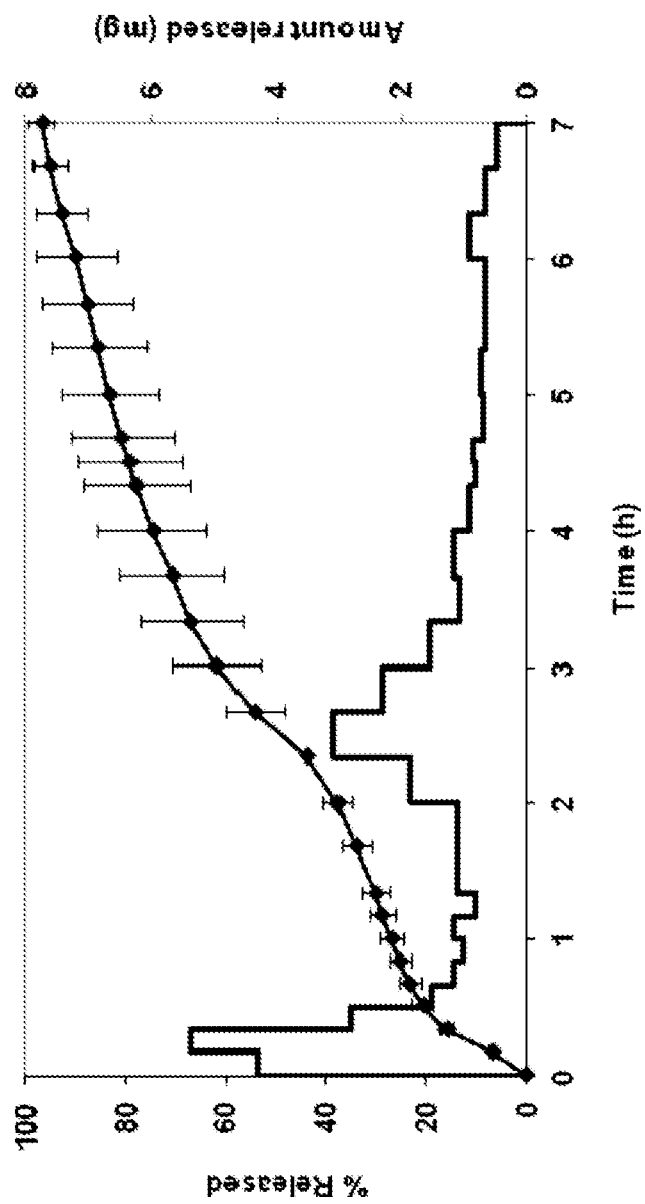
FIG. 7 is a graph illustrating continuous monitoring of samples showing timed (controlled) release.

The concentration of drug is then assessed using any appropriate analytical technique such as UV-Visible spectroscopy, high pressure liquid chromatography (HPLC) or mass spectrometry. FIG. 6 illustrates concentration of a drug over time. See *Inter. J. Pharmaceutics* 388(2010) 287-294. In addition to sampling periodically, the sample may be monitored continuously via flow through cells as seen in FIG. 7.

Definitions

Cataract. Cataracts are changes in clarity of the natural lens inside the eye by the accumulation of turbulent fluid, which gradually degrades visual quality. Cataract surgery can be a very successful treatment for the restoration of vision. During surgery, the clouded lens, i.e. turbulent fluid, is removed and replaced with a clear, intra ocular lens.

Intra Ocular Lens (IOL). An intraocular lens (IOL) is a lens implanted in the eye used to treat cataracts or myopia. Thick eye glasses or special contact lenses that were previously required to see after cataract surgery have been replaced by several types of IOL implants. The main function of an IOL is to focus light on to the retina. Light rays are then converted into electrical impulses that travel to the brain, where they are then converted into images.

IOLs are round, corrective central portions of the lens with two arms or haptics. IOLs allow investigations of the sustained release of therapeutic levels of drugs for a desired period of time, thus overcoming the Blood Retinal Barrier (BRB) associated with systemic drug delivery. Varieties of IOL styles available for implantation include: monofocal lens; toric lens; and multifocal lens.

Structure of IOL. (FIG. 1) The center viewing zone is called the optic. This is a clear, round disc measuring 5.5 to 6.5 mm in diameter. On opposite sides of the optic, there are two flexible struts present, which are called Haptics. These Haptics act like tension loaded springs to automatically center the lens within the compartment.

Drugs Used. The drugs used include sulfate drops, antibiotics (antibacterials) and anti-inflammatory drugs. An example of an antibacterial drug is Vancomycin. An example of an anti-inflammatory drug is Alclofenac. The drugs to be used also include hydrophilic and hydrophobic drugs. Hence, reverse micelle and liposomes are used for encapsulation of the drug.

More particularly, ocular drugs include Bevacizumab (Avastin), Ranibizumab (Lucentis), Pegaptanib (Macugen), Aflibercept (Eylea), Atropine, Flurbiprofen, Physostimine, Azopt, Gentamicin, Pilocarpine, Bacitracin, Goniosol, Polymyxin B, Betadine, Gramicidin, Prednisolone, Betaxolol, Humorsol, Proparacaine, Betoptic, Hylartin, Propine, Brinzolamide, Hypertonic NaCl, Puralube, BSS, Indocyanine Green, Rose Bengal, Carbachol, Itraconazole, Sodium Hyaluronate, Cefazolin, Latanoprost, Suprofen, Celluvisc, Mannitol, Terramycin, Chloramphenicol, Methazolamide, Timolol, Ciloxan, Miconazole, Tobramycin, Ciprofloxacin, Miostat, Triamcinolone, Cosopt, Muro 128, Trifluridine, Demecarium, Neomycin, Tropicamide, Dexamethasone, Neptazane, Trusopt, Dipivefrin, Ocuflo, Vidarabine, Dorzolamide, Ofloxacin, Vira-A, Epinephrine, Oxytetracycline, Viroptic, Fluorescein, Phenylephrine and Xalatan."

Problems with Ocular Therapy: Problems with ocular therapy include multi drug resistance and systemic toxicity due to high doses. The method outlined here would obviate the latter problem because the drugs will be released slowly.

Liposomes: Liposomes are water-in-oil-in-water (w/o/w) emulsions with closed bilayer membranes that contain an entrapped aqueous volume. Liposomes encapsulate both hydrophilic and hydrophobic molecules. Liposomes are of two types: multilamellar vesicles (MLVs) and large unilamellar vesicles (LUVs).

Encapsulation of Drugs: Hydrophilic drugs are encapsulated in water in oil emulsions. The water in oil emulsion is titrated against the aqueous phase and surfactant, which leads to the formation of liposomes (i.e. w/o/w emulsion).

Liposome Procedures: Unilamellar (1-3) and multilamellar liposomes are prepared by standard methods and from commercially available phospholipids such as phosphatidylcholine and phosphatidylethanolamine. The drug-encapsulating liposomes are used as a liquid suspension (for intraocular injection) or attached to the surface of an IOL, stent or contact lens. Attachment is achieved by covalent tethering (4) or by embedding in a biocompatible hydrogel. (Lin and Marra, 2012; Mawood et al. 2012).

Preparation of water in oil emulsion (Inverted Micelles): Oil was heated gently on a low flame. Surfactant was then added to the oil phase and low heating was maintained with continuous stirring. Aqueous drug solution was added dropwise to this phase, maintaining low heat and continuous stirring.

Sustained Release (SR) Technology. Slow release of a drug over a time period may or may not be controlled release. Drug concentration varies with time because the initial release of a drug is sufficient to provide a therapeutic dose soon after the administration, and then there is a gradual release over an extended period.

Fluorescence intensity studies using inverted micelles on IOLs showed that there is an increase in the intensity with respect to time. Increase in fluorescence intensities supports the prolonged release of the drug at a predetermined rate by maintaining a constant drug level at a specified period of time.

Advantages of SR: The advantages of sustained release technology include uniform release of drug substance over time, reduction in frequency of intakes, reduced side effects, and better patient compliance.

IOL Coating. An important part of the sustained release forms are biodegradable, highly flexible polymeric coatings with sustained release effect.

Purpose of coating: The purpose of the IOL coating includes: obtaining functional coats, i.e. coats that are stable and slowly release the drugs, providing chemical stability, and enhancing patient acceptance.

Preparation of the coated formulation: A polymer was dissolved in a suitable carrier solvent. A water-in-oil (w/o) emulsion was added and coated. Coated formulations were then applied on the IOL implants. Coated IOL implants were then placed in a suitable buffer solution.

Sustained drug delivery using IOLs for the treatment of AMD is contemplated. The technique is simple, non-invasive and should improve the ocular bioavailability, therapeutic efficacy and patient compliance of the treatment substance.

Abbreviations for Formulation Compositions and Instruments Used

PC—Phosphatidyl choline
PE—Phosphatidyl ethanolamine
PG—Phosphatidyl glycerol
PE-PEG 2000—1,2-dimyristoyl-sn-glycero-3-phosphoethanolamine-N-[methoxy(polyethylene glycol)-2000] (ammonium salt)
Chol—Cholesterol
DLS—Dynamic Light Scattering
TEM—transmission electron microscopy
SAXS—Small angle X-ray Scattering
BC—Beta Carotene
CX—Cantaxanthin Summary of Methods to Prepare Lipid Vesicles (Ranging from 30 NM to 50 µM)

Part I Diameter: 30 nm-50 nm (SUV-Small Unilamellar Vesicle)

The shelf-time of these small lipid vesicles is very short due to their high surface tension. They are usually used immediately after preparation.

Two methods can be used to produce them.

Method 1: Extrusion

The same procedures as in Part II, but choose a PC membrane with smaller pore size (30 nm-50 nm).

Method 2: Sonication

Make stock solution: dissolve DMPC lipids in chloroform initially to make 8 mg/ml concentrated lipid solution (stock solution).

Sample solution: use ~0.23 g of stock solution, which should give ~1.2 mg of DMPC lipid, and dilute the concentrated stock solution in more chloroform.

Evaporation: Blow-dry the dilute lipid sample using nitrogen for 2 hours to evacuate the solvent of chloroform.

Hydration: add ~1.2 ml PBS buffer to hydrate the dry lipid sample as soon as the chloroform is all evaporated.

Sonication: Insert the titanium-tip sonicator inside the lipid suspension and do sonication. Vesicle size and distribution depend on sonication power, frequency and time.

Part II Diameter: 80 nm-800 nm (LUV-Large Unilamellar Vesicle)

The typical method to make LUV is "extrusion." The detailed procedures are summarized as follows. Note that vesicles produced by this method are usually more polydisperse at larger sizes.

1. Make stock solution: dissolve DMPC lipids in chloroform initially to make 8 mg/ml concentrated lipid solution (stock solution).

2. Sample solution: use ~0.45 g of stock solution, which should give ~2.4 mg of DMPC lipid, and dilute the concentrated stock solution in more chloroform.

3. Evaporation: Blow-dry the dilute lipid sample using nitrogen for 2 hours to evacuate the solvent of chloroform.

4. Hydration: add ~2.4 ml PBS buffer to hydrate the dry lipid sample as soon as the chloroform is all evaporated.

5. Incubation: Place the sample container in a sand bath at ~40 deg. C. for 2 hours. During the 2 hours of incubation, mix the sample once every 10 minutes using a vortexer.

6. Freeze/thaw: Immerse the sample in liquid nitrogen followed by boiling water for 5 cycles totally.

7. Extrusion: assemble the membrane inside the extruder:
(1) Wet the Teflon piece with buffer;
(2) Place 2 pieces of membrane support in the center of the Teflon piece;
(3) Add a drop of water before putting the PC membrane;

(4) Put the PC membrane with proper pore size on the taller piece of the holder;

(5) Add a drop of buffer on top of the membrane;

(6) Place 2 pieces of Teflon holder together;

(7) Turn up the heater underneath the extruder to above Tm, and place the syringe on the heater to warm up;

(8) Fill the lipid solution into the syringe, and extrude 11 times;

(9) Eject the extruded sample from the acceptor syringe. The solution should look clearer than that before extrusion.

8. Cleaning: The Teflon piece, o-ring and syringe should be rinsed with copious 2-propanol and DI water after use. Otherwise the residues will contaminate your next sample.

Notes:

In order to control the pH of the buffer solution, $NaH_2PO_4$ and $Na_2HPO_4$ are used as phosphate salt to make pH=6, $[PO_4^{3-}]$=10 mM PBS solution. The molar ratio of the two salts are ~7.5:1.

Don't use the same membrane for more than 3 ml of solution.

Part III Diameter: 1 µm-50 µm (GUV-Giant Unilamellar Vesicle)

Bearing in mind that even though there are various methods to make GUVs, the key principle is similar, encouraging dried lipid films to swell and form giant vesicles. Here are five typical methods of making GUV.

Method 1: LUV Fusion

As is well known, LUVs are not stable in suspension because of vesicle fusion with each other. This method is taking the advantage of inter-vesicle fusion to form giant vesicles. This method is very simple, but it is inefficient to produce vesicles larger than 10 µm.

1. Prepare LUV: See Part II for details.
2. Prepare GUV: Keep the LUV suspension at room temperature for 1~2 days. Giant vesicles with diameter less than 10 µm formed massively in the suspension.

Figure 8:
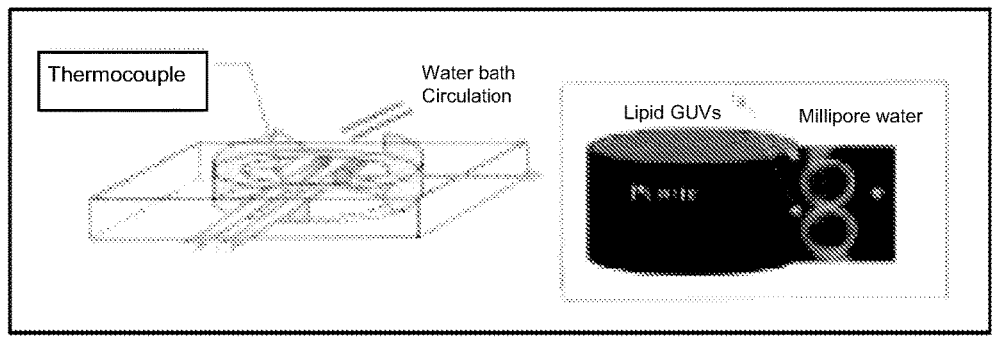
FIG. 8 shows apparatus used in liposome electroformation.

Method 2: Electroformation—Pt Wire (Gratton, et al.)—(FIG. 8)

This method is widely used to produce GUVs with various components and inclusions. Advantages: (a) vesicle size is well controlled by tuning the electric field; (b) detaching vesicles from the Pt wires is possible; (c) transfer of the GUVs to other medium from the open chamber; (d) all GUVs are unilamellar. Disadvantages: (a) Time-consuming—each sample preparation needs many hours to clean the chamber; (b) Inefficient—just a few GUVs can be produced each time due to the small amount of lipids used for each sample; (c) It is tricky to add lipid stock solution onto the Pt wires.

1. Clean the Chamber: Sonicate the chamber in soap, ethanol and DI water for 1 hour respectively. Then dry it using nitrogen.
2. Spread Lipids: Add 3 µl lipid stock solutions (0.2 mg/ml) to each wire evenly. Keep the whole setup under nitrogen for 2 hours to evacuate the organic solvents.
3. Glue the Cover Glass: Use epoxy adhesive to seal the chamber bottom window with cover glass.
4. Add Water/Buffer: 2 ml water is enough and make sure there is no leakage of the chamber.
5. Lipid Hydration: Turn on the electric field (10 Hz, 3 V) for 90 minutes. GUVs formed along the Pt wires.

Method 3: Electroformation—ITO Glass (Schwille, et al.)

This method is a derivative of method 2; using ITO glass to replace Pt wire. Compared with method 2, it has the advantages of (a) being much faster—there is no need to clean the chamber or other devices before sample preparation; (b) producing many GUVs each time; (c) making GUV patterning on ITO-coated glass surface possible. Disadvantages: (a) Because the two ITO glasses are glued together, it is hard to collect GUVs and transfer them somewhere else.

1. Clean ITO-Coated Glass: Rinse the glass with 2-propanol and acetone.
2. Spread Lipids: Add lipid stock solutions (0.2 mg/ml) onto one of the ITO glass surface. Keep it under nitrogen for 2 hours to evacuate the organic solvents.
3. Add Water/Buffer: Add buffer solution to the dried lipid films.
4. Glue the Two ITO Glasses: Use epoxy adhesive to glue the two glasses together.
5. Lipid Hydration: Turn on the electric field (10 Hz, 3 V) for 90 minutes. GUVs formed on the ITO glass.

Figure 9:
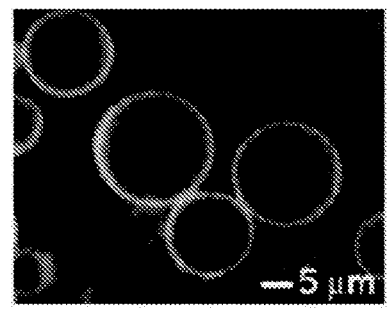
FIG. 9 shows results of dehydration-rehydration of lipid vesicles.

Method 4: Dehydration-Rehydration (Orwar, et al.)—(FIG. 9)

Advantages: (a) This method is very simple; (b) It takes several minutes to form GUVs; (c) Most of the GUVs are unilamellar. Disadvantages: (a) GUV size is relatively small, ~10 µm; (b) it is hard to remove vesicles from the substrate surface;

1. Prepare LUV: See Part II for details.
2. Dehydrate LUV: Add a droplet of the LUV suspension (5 µl) onto a hydrophilic substrate such as quartz and glass. Place the substrate into a vacuum oven at room temperature of 10 minutes to dehydrate lipid vesicles.
3. Rehydrate LUV: After the LUVs are dry, add 5 µl buffer solutions to rehydrate the lipid membrane. GUVs appear in couple of minutes.

Figure 10:
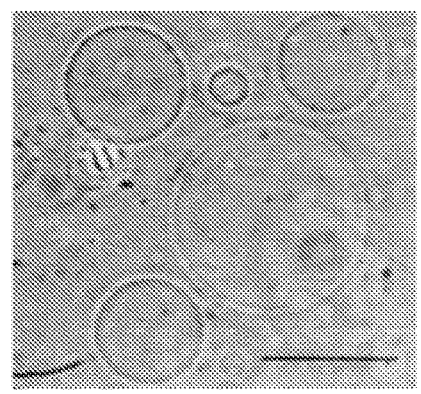
FIG. 10 shows results of sucrose hydration of lipid vesicles.
Figure 11:
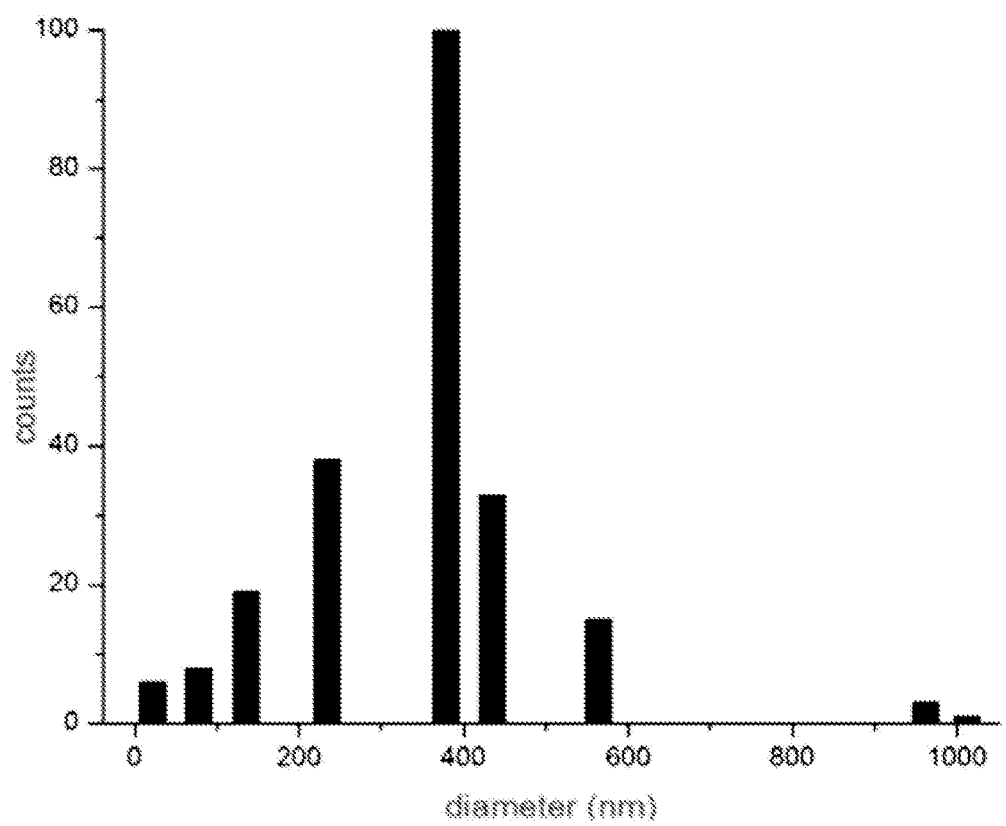
FIG. 11 shows the average hydrodynamic diameter of the liposomes determined by Dynamic Light Scattering® using Brookhaven BI-200SM Research Goniometer and Laser Light Scattering System; the size distribution obtained is as shown.
Figure 12A:
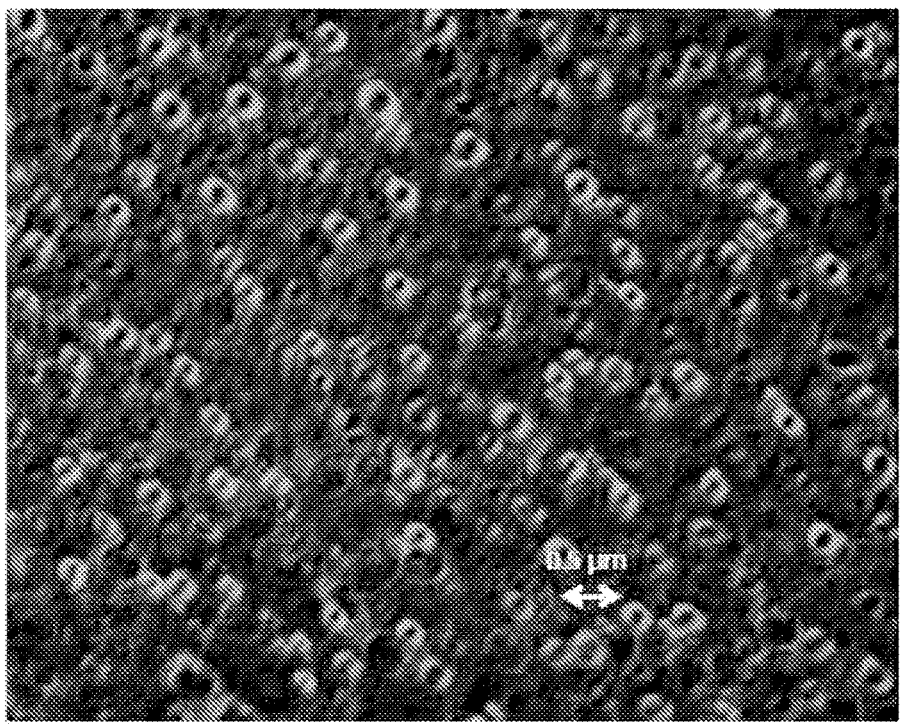
FIG. 12 shows that the liposomes were visualized: (A) 0.5 µm; (B) 1 µm; (C) 5 µm.
Figure 12B:
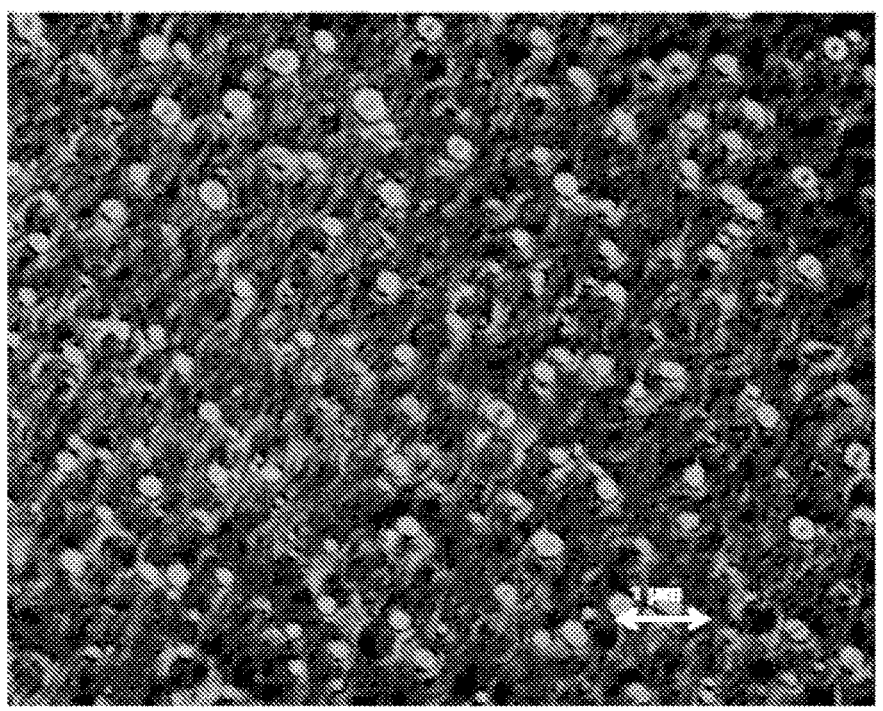
Figure 12C:
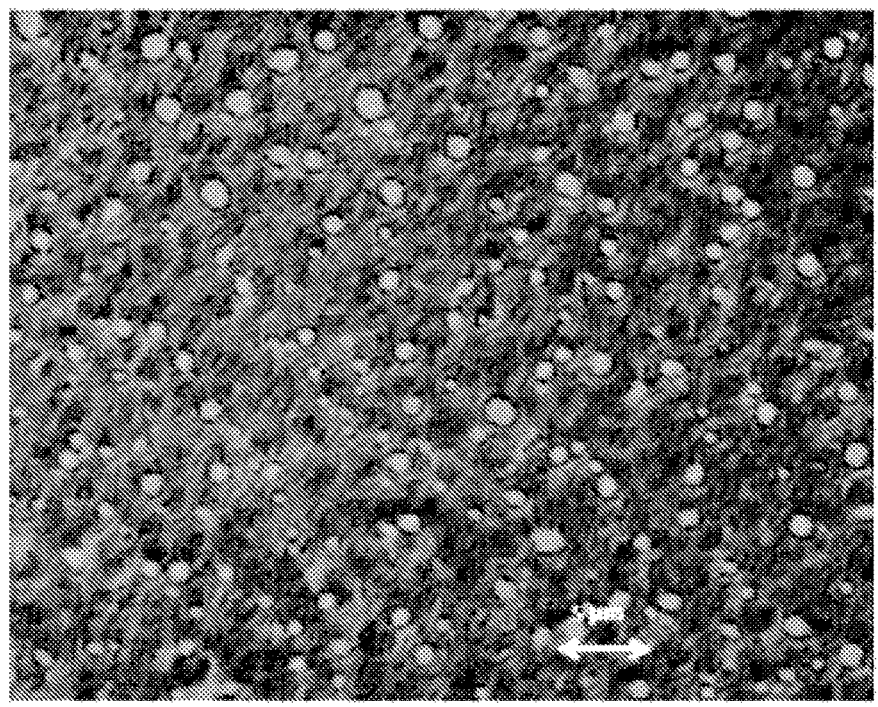
Figure 13:
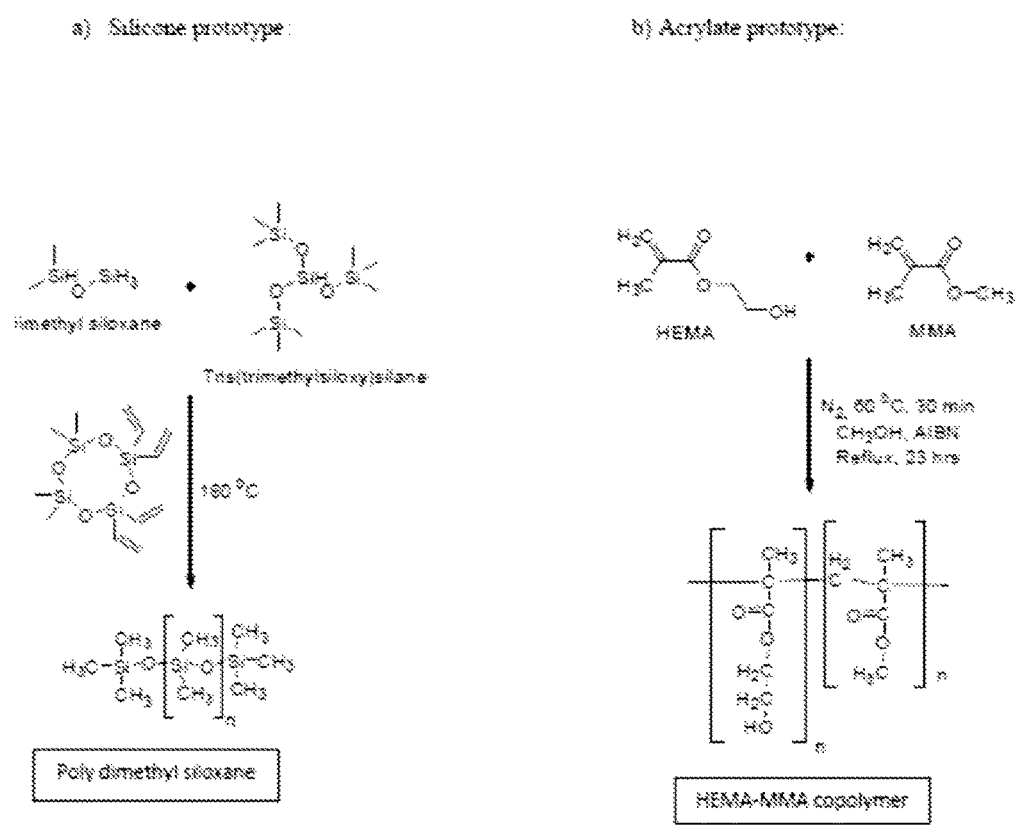
FIG. 13 shows the preparation of prototype contact lenses: (A) silicone; (B) acrylate.

Method 5: Sucrose Hydration (Kinosita, et al.)—(FIG. 10)

Advantages: (a) Efficient—each sample preparation produces many GUVs; (b) It is very easy to generate osmotic pressure to the GUVs by controlling internal and external solute concentration. Disadvantages: (a) It uses too much sucrose, 100-500 mM, which may affect other measurements; (b) GUVs are not always unilamellar.

1. Make stock solution: dissolve DMPC lipids in chloroform initially to make 8 mg/ml concentrated lipid solution (stock solution).
2. Sample solution: use ~0.45 g of stock solution, which should give ~2.4 mg of DMPC lipid, and dilute the concentrated stock solution in more chloroform.
3. Evaporation: Blow-dry the dilute lipid sample using nitrogen for 2 hours to evacuate the solvent of chloroform.
4. Hydration: add ~2.4 ml sucrose solution (100-500 mM) to hydrate the dry lipid sample as soon as the chloroform is all evaporated.
5. Incubation: Keep the sample container in a vacuum oven at ~37 deg. C. for overnight. GUVs will form and float in the suspension.

Preparation of w/o/w/o Emulsion (a) 500 ml of Triton X-100 (0.485 mg) was dissolved in 4 ml of ethyl acetate to form organic/oil phase.

(b) a hydrophobic drug, i.e. 23 uM or 0.0948 gm in 10 ml of fluorescein, was prepared and 1 ml of water phase was taken from that solution.

(c) water phase was titrated drop by drop into organic phase by constant stirring to form w/o emulsion.

(d) heat the above emulsion until left with 3 ml of emulsion.

(e) 500 mg of PVA was dissolved in 40 ml of water. The w/o emulsion from (d) was added drop by drop to form w/o/w emulsion.

(f) 500 ml of Triton X-100 was dissolved in 10 ml of ethyl acetate. The liposomes from 9(e) were added to final organic phase.

Observation: milky white emulsion was formed and the colour of fluorescein solution disappeared.

Chitosan Coating Solution to Form Semipermeable Membrane (a) 200 mg of chitosan was dissolved in 40 ml of 2% arctic acid solution.

(b) 1 ml of PEG was added to this solution.

(c) the solution was heated at 90° C. to form a viscous fluid.

(d) the product was sonicated for 1 hour.

Addition of nonparticle solution into the above mixture gave a homogenous solution.

Preparation of o/w Emulsion 1) dissolve riboflavin in ethyl acetate and prepare an organic phase by adding cellulose derivatives and heating at 50° C.

2) dissolve carbomer (0.4 g) in 20 ml of water and heat at 50° C. to form the aqueous phase.

3) add organic phase to the aqueous phase in a drop-wise manner under high shear.

4) heat the solution above 78° C. to remove ethyl acetate;\

5) final solution is clear.

Particle Size Measure

1) DLS was used 2) particle size ~400 nm.

Need to change surfactant.

Preparation of w/o/w Microemulsion 1) fluorescein and carbomer were dissolved in water and heater.

2) this aqueous phase was poured in a drop-wise fashion into the oil phase containing vit-F and cellulose.

3) finally the w/o emulsion was added in a drop-wise manner into an aqueous phase containing polyvinyl alcohol.

Observation: w/o emulsion was good; w/o/w emulsion was not stable→may be because of less surfaction.

Preparation of Water Soluable Citosan by N-Acetylation (a) 1 gm of chitosan was dissolved in 25 ml of 2.8% acetic acid and then 25 ml of ethanol was added.

(b) Little pyridine was dropped into the mixing solution until the solution because clear.

(c) Excess acetic anhydride was added.

(d) The solution was stirred at 25° C. for 2 hours.

(e) Formation of a clear semisolid can be observed.

(f) The reaction mixture was precipitated with ethanol.

(g) The precipitate was filtered out and washed with acetone to remove excess reactant.

N-acetylated chitosan was dried at 50° C.

Lypophilization Method (a) equimolar conc of riboflavin and HP-βCD and 0.28 gm of riboflaving)

(b) mixture was agitated for 48 hours at room temperature and filtered through 0.45 μm membrane filter and the filtrate was lyophilized.

Evaporation Method (a) equimolar proportion of riboflavin in ethanol was added dropwise to HPβCD aq. Soln. the solution was stirred for 2 hours using a magnetic stirrer.

(b) obtained soln. was evaporated under vacuum at 50° C. The residue was finally dried at 40° C. for 24 hours.

$H^1$ and $c^{13}$ NMR of Chitosan and HP-β-CD

Phase Solubility Study (a) 50 mg of riboflavin was mixed with different concentrations of HP-β-CD (5, 10, 15, 20, 25, 30 mM)

(b) the mixture was stirred on rotary shaker for 72 hours at 37° C.

(c) after reaching equilibrium, samples were filtered through a 0.2 μm filter and suitably analyzed using UV-vis spectrophotometer.

(a) Preparation 1:

10 ml Chitosan soln (2 mg/ml) in 2% acetic and 4 ml TPP soln. (2 mg/ml) in D.I. water.

The above solutions were mixed and turbidity observed. On subjecting this solution to Dynamic Light Scattering, particles in the rage of 3000 nm were observed.

(b) Preparation 2:

60 mg of chitosan in 20 ml of 2% acetic and 1 ml of 1% TPP adjusted pH 3 using HCl.

The above solutions were mixed and turbidity was observed. Need to increase the volume of TPP soln.

Phase Solubility Study:

(a) 50 mg of riboflavin was mixed with different concentrations of methyl-β-cyclodextrin (5, 10, 15, 20, 25, 30 mM).

(b) The mixture was stirred for 72 hrs. on a rotary shaker at 37° C.

(c) After reaching equilibrium, samples were filtered through 0.2 μm membrane filter & analyzed using a spectrophotometer.

HPBCD—0.0219 gm (5 mm)

0.0438 gm (10 mm)

0.657 gm (15 mm)

0.0876 gm (20 mm)

0.1095 gm (25 mm)

0.1314 gm (30 mm)

Formulation:

(a) Equimolar concentration (0.05M) of riboflavin (0.188 gm) was mixed with methyl Betacylodextrin (0.66 gm) and stirred for 48 hrs. with agitation in 50 ml of water.

(b) The mixture was filtered through a 0.2 μm membrane filter and analyzed using UV-vis spectroscopy.

Determining the Hydrodynamic Diameter of Nanoparticles:

Technique: Dynamic Light Scattering

Temp: 25° C.

Solutions: Riboflavin nanoparticles (Cyclodextrin). Control cyclodextrin solution.

Results: Nanoparticles—129 nm. Cyclodextrin—13.9 nm

Methylcyclodextrin & Riboflavin (a) 50 mg of riboflavin was mixed with 5, 10, 15, 20, 25, & 30 mM methyl cyclodextrin in 3 ml of water.

(b) The solutions were left to equilibrate for 3 days on a shaker.

(c) After filtration, the solutions were analyzed by UV-vis spectroscopy.

Preparation of Niosomes

Different niosomal preparations were made using lipid hydration.

Molar concentrations of 1:1, 3:2, 8:7, 7:8 ratios of Tween 80 & cholesterol were dissolved in 9 ml of chloroform/methanol mixture (6 ml:3 ml).

The solvent was rotovapped off to leave a thin file.

The film was hydrated using dye solution for 24 hrs.

Result: 1:1 ratio gave a particle size of 212 nm. (from DLS data)

UV-Vis for Phase Solubility (Riboflavin)

The methyl β-cyclodestrin & hydroxy propyl beta cyclodextrin solutions were filtered.

The UV-vis absorption spectrum was obtained for each solution.

The data was used to plot a phase solubility curve for both the cyclodextrine.

| Result: | Solubility for methyl β CD - 31.07 mg/ml. |
|---|---|
| | Solubility for HPβ CD - 33.03 mg/ml. |

Hyaluronic Acid—Chitosan Nanoparticles

Prepare 0.069 l/l w/v chitosan solution in 4.6 mM HCl at pH 5 by adding IM NaOH. 0.0138 gm of chitosan was dissolved in 20 ml of 4.6 mM HCl.

The final solution was stored in refrigerator to check the stability.

Phase Solubility of Ofloxacin Samples:

| Methyl β-CD- | 5 mM-0.0133 gm | All in 2 ml |
|---|---|---|
| | 10 mM-0.0266 gm | |
| | 15 mM-0.0399 gm | |
| | 20 mM-0.0533 gm | |
| | 25 mM-0.0666 gm | |
| | 30 mM-0.0799 gm | |

50 mg of ofloxacin was added to each sample and then shaken for 72 hrs to attain equilibrium.

Result: Solubility was found to be 35.04 mg/ml.

Mucoadhesive Chitosan Nanospheres:

Ofloxacin is very soluble in acidic pH.

Chitosan was dissolved in 2% autic acid solution at pH4.

50 mg of ofloxacin was dissolved in the above solution.

To this solution, Sodium TPP solution was added in a drop wise manner until the solution becomes slightly cloudy.

Result: Average particle size was found to be 413 nm.

Baking PDMS Lens:

6.2 gm of Sylgard 184 Silicone elastomer base was taken & 620 Ml of curing agent was added.

The mixture was property degassed for removal of air bubbles.

The mixture was spread on a wax paper & baked for 2 hrs. at 200° C.

The layer was too thin to remove from wax paper.

Chitosan—HA Nanoparticles:

The chitosan nanoparticles prepared on 10/9/12 were coated using HA.

2 ml of 0.05% w/v nanoparticles in 0.1 M acetate buffer at pH 5 were slowly added under vigorous stirring (30 min., 12001 pm) to 2 ml of acetate buffer containing 0.15 wt % of HA.

Dialyze against 10 mM PBS at pH 6.

Trial for Chitosan Nanoparticles:

(a) 0.5% w/v chitosan in 1% arctic and solution was prepared—Solution 1.

(b) Adjust the pH of soln. 1 to 4.1 using 10 N NaOH.

10 ml of 2.5 mg/ml TPP solution was prepared—Soln. 2.

Solution 2 was added in a drop wise manner to 30 ml of solution 1.

This mixture was stirred at 1000 rpm for 15 minutes.

Cross Linked Chitosan Hydrogels:

5 samples of 0.1 g chitosan each were dissolved in 7 ml of '1% glacial arctic acid solution.

Add 1.5, 2.5, 3.5, 4.5 & 5.5 ml of 5 mol/Lit HCHO (3 mg in 100 ml) solution into each sample.

Water was added to make up a volume of 12.5 ml.

Cross linking time is between 1 hr. and 2 days.

Modification of Lysine & Arginine Using MGO:

0.1464 gm of lysine was mixed with 10 ml of water & 50 mM MGO was added.

Similarly 0.174 g of arginine was used to make another solution.

The solutions were incubated at 37° C.

Vit-E Barrier Coating:

This was used for hydrophobic drugs which are soluble in alcohol.

Excess vit-E was dissolved in 5 ml of alcohol & the drug was dissolved in this solution. The solution is coated on a surface & left to dry at 100° C. for 1 hr. to get a uniform coating.

Liposome Preparation:

Mix 100 mg of egg phosphatidyl choline, 40 mg of cholesterol & 10 mg of phosphatidyl glycerol in 5 ml of 2:1 chloroform-methanol mixture (3.3:1.7 ml).

Rotovap the solution at 60° C. to get a thin film.

1 mg/ml Rhodamine solution was used (f ml) & mixed vigorously with the film for 30 minutes.

The suspension was left for 24 hrs.

DLS of Liposomes:

Particle size was found to be 379 nm. (Size distribution profile in data folder.)

Preparation of Silicone Prototype Lenses:

The silicone base & the curing agent were mixed in 9:1 ratio & air bubbles were removed.

The mixture was heated in the oven to set at 180° C. for 2 hrs.

The silicones were formed.

Observation—Silicone sticks to glass. Need to change base to prepare the lenses.

Preparation of Niosomes:

1:1:1 ration of fluorescein, span 20 & cholesterol, each 200 mg was dissolved in 6 ml of diethyl ether. It was mixed with 2 ml of methanol containing dye after rotovaping the ether. The solution was left to equilibrate for 24 hrs. Particle size was found to be 565 nm Extraction of L-Crystallin:

Trials for Niosomes:

| Trial | Dye (mg) | Span 20 (mg) | Cholesterol (mg) |
|---|---|---|---|
| 1 | 200 | 200 | 200 |
| 2 | 200 | 300 | 200 |
| 3 | 200 | 400 | 200 |
| 4 | 200 | 200 | 300 |
| 5 | 200 | 300 | 300 |
| 6 | 200 | 400 | 300 |

Result: 1:1.5:1 ratio of dye:span:cholesterol gave the least particle size & are pretty stable.

Vitamin E barrier coating: ethanol solutions were prepared at cones of 0.05, 0.1, 0.15 g/ml ethanol and then the dye was dissolved in the solution.

The solution was mixed with 0.1 ml of PEG as plasticizer.

The coating solution was introduced on the glass slides and coated by spin coating.

The slides were dried using vacuum drying.

(Note: Never use the oven.)

Preparation of HEMA—MMA Copolymers:

14 ml of HEMA & 5.3 ml of MMA were added to 200 ml of THF under N2.

0.2995 g of AIBN was added to solution after 20 min. of stirring & the reaction temp. was raised to 60° C. for 23 hrs.

The excess THF was rotovapped and product was precipitated in diethyl ether.

The ppt. was mixed in methanol and again ppt. with ether.

Result: The product obtained was 12.93 gm.

Cellulose Derivative Coatings:

Cellulose Derivative Plasticizer.

a) Methyl cellulose (MC) PEG
b) Hydroxyl propyl methyl cellulose (HPMC) PEG
c) MC ethylene glycol
d) HPMC ethylene glycol 10% w/v solutions of cellulose derivatives with 2.5% plasticizer were prepared and located on to the prototype lenses.

Results PEG works better.

Trial for Chitosan Nanoparticles

Procedure:— a) 3% acetic acid was prepared
b) Different concentrations of acidic chitosan solutions were prepared, 2 mg/ml, 1 mg/ml, 0.7 mg/ml, 0.5 mg/ml, 0.3 mg/ml, 0.1 mg/ml
c) Different concentrations of TPP solutions were prepared—0.2, 0.4, 0.6, 0.8 and 1.0 mg/ml
d) Combinations of both the solutions were prepared and sonicated at 20 min.
e) These solutions were centrifuged at 15000 rpm for 10 min.

Microscopy of the Coatings Using Bright Field Illumination a) Water soluble chitosan coating
b) Vitamin E barrier coating
c) Methyl cellulose coating (with PEG)
d) HPMC coating (with PEG)
e) Hyaluronic acid coating (with PEG and PVA)

The coating solutions prepared, were coated onto glass slides by spin coating. The samples were let to air dry/vacuum dry depending on the material used.

Preparation of Riboflavin—Chitosan Nanoparticles a) 3 mg/ml of riboflavin was added to the chitosan solution (20 ml).
b) 3.5% w/v of chitosan solution was prepared using 2% acetic acid solution
c) 15 ml of 0.4% STPP soln. was added in a dropwise manner to the chitosan solution
d) A suspension was formed Dialysis of Lysine Dimers Changed the buffers for dialysis after every 12 hours.

Dialysis of α-Crystalline

Desalted the sample against MQ water after every 12 hours

Preparation of BSA—Chitosan Nanoparticles a) 100 mg of BSA was dissolved in the chitosan solution
b) 3.5% w/v of chitosan solution was prepared by dissolving chitosan in 2% acetic acid soln.
c) 15 ml of 0.4% STPP soln. was added drop-wise
d) A clear solution was formed.
e) It has to be further visualized using TEM for formation of nanoparticles Dialysis of Lysine Dimers Using Phosphate Buffer at pH 7.6

Dialysis of α-Crystalline

Chitosan—citric acid coating soln.

Different concentrations of citric acid ranging from 25% to 55% was added into 10 ml of acetone. 10-20% of PEG and 30-35% of chitosan were added. Citric acid, PEG and chitosan constitute up to 4% of the total ingredients added to acetone. Citric acid is added to create an acidic environment to dissolve small amounts of chitosan.

MS of Lysine

Equilibrate the column for 1 hour.

Inject 20 ml of the lysine sample.

Lysine sample was not soluble in acetonitrile so use water.

Flow rate—0.2 ml/min; Gradient—100 to 50% water.

No results because MS was running in negative ion mode.

Coating Solution (Chitosan Membrane)

a) Prepare a solution of chitosan in 2% glacial acetic acid to produce 3-5% w/v solution and add 0.5 ml of PEG-200.
b) Homogenize the solution at 2000 rpm.
c) Degar by sonication at 25° C. for 20 min.
d) The chitosan soln. was cast on a polycarbonate petri dish and dried at 45° C. for 48 hours.

Preparation of Chitosan-Acetone Coating Solution

Dissolve 40 mg of chitosan in 10 ml of 1% acetic acid solution by constant stirring.

Take 5 ml. of the above solution and add 5 ml of acetone.

It produces a homogenous mixture.

Now add 0.5 ml of PEG to work as a plasticizer

Store in refrigerator.

Preparation of Liposomes Using Ethanol Injection Method:

1) Make 2 mg/ml soln. of fluorescein with 0.1 ml of surfactant & heat up to 60° C., with continuous stirring.
2) Make a lipid mixture of PC: cholesterol (5:2) & dissolve in 10 ml absolute alcohol at ~60° C.
3) Quickly inject into a well-stirred aqueous phase & keep for 30 mins. flask & ethanol was removed by rotovap at 40° C.
4) The liposome mixture was transferred to round bottom.
5) The obtained MLVs are sonicated for 1 hr. to get ULVs.
6) The final solution was extruded & lyophilized.

Formulation:

Method Used: Ethanol Injection

| Ingredients | Quantities |
| --- | --- |
| Phosphatidyl choline | 36 mg |
| Phosphatidyl ethanolamine | 6 mg |
| Cholesterol | 36 mg |
| Ethanol | 3 ml |

Mix all the ingredients above at 60° C. to make stock coln.

Formulation 1:

1) Add the lipid stock solution (1 ml) to 2 ml of 2 mg/ml fluorescein solution at 60° C. & mix it for 30 min at very high speed.
2) Rotovap ethanol to get MLVs. Extrude at least 8 times to get ULVs & then lyophilize.

Formulation 2:

1) Add 6 mg of PEG to lipid stock (1 ml) & then inject into 2 ml of 2 mg/ml dye solution at 60° C. & repeat the procedure above.

Formulations:

Method Used: Ethanol Injection

Formulation:

| Ingredients | Quantities |
| --- | --- |
| 1) PC | 30 mg |
| 2) Cholesterol | 10 mg |
| 3) Vit E | 10 mg |
| 4) PEG | 10 mg |
| 5) Ethanol | 2 ml |
| 6) Fluorescein | 100 mm in 5 ml water |
| 7) Vit F | 10 mg |
| 8) Oleic acid | 5 ml |

Formulation 3:
Mix 3 & 4 at 60° C. To it, add 1, 2 & 5. Prepare a suspension, rotovap, sonicate & extrude.
Formulation 4:
Mix 7, 8 & 4 at 60° C. To it, add 1, 2 & 5. Prepare a suspension, rotovap, sonicate & extrude (30 min).
Lyophilize the samples.
A) Formulation 5:
PC—22.56 mg
DPPE—2.38 mg
DPPG—2.56 mg
CH—2.5 mg
Dissolve the lipids & CH in approx. 1 ml of chloroform & 1 ml of methanol. Slowly remove the organic solvent at 50° C. wing rotovap.
Add 5 ml of 1 mm fluorescein (drug) in 0.33 mannitol solution & swirl the flask to form a homogenous suspension.
Sonicate the liposomal dispersion for 5 min in bath sonicator.
Measure the absorbance & compare it 1 mm drug/dye solution.
Freeze the soln. at −70° C. for 30 min & thaw at room temp.
Repeat the above step at least 3 times.
Finally lyophilize the samples.
Measure particle size using DLS.
Results: Absorbance of dye solution—0.6 at 494 nm. Absorbance of liposome—0 at 494 nm.
B) Dialysis of modified α-crystallin—Day 1
A) Formulation 6:
Preparation of Liposomes containing proteins
PC—100 mg
CH—12.5 mg
Tocopherol—0.5 mg
HSA—10 mg
Dissolve the lipids & Vit E in methanol: chloroform (1:1) & rotovap to get a thin film (between 30-60 min) at 45° C.
Add HSA solution in phosphate buffer ($p^H$ 7.4) by vigorous agitation for hydration of the lipid layer.
Subject to 3-5 freeze thaw cycles followed by extrusion.
Finally lyophilize the sample after DLS measurement.
B) Dialysis Day 2
C) DLS of formulations 3 & 4:
Vit E liposomes—mean particle diameter 9 μm

PUBLICATIONS CITED

1. Hamai, C. et al; "Effect of Average Phospholipid Curvature on Supported Bilayer Formation on Glass by Vesicle Fusion" Biophys. J. (2006), 90; 1241-1248.
2. Cevc, G. and Richardsen, H. "Lipid vesicles and membrane fusion" Adv. Drug Delivery Rev. (1999), 38: 207-232.
3. Moscho, A. et al "Rapid preparation of giant unilamellar vesicles" Proc. Natl. Acad. Sci. (1996), 93: 11443-11447.
3. Yoshina-Ishii, C. et al "General method for modification of liposomes for encoded assembly on supported bilayers" J. Am. Chem. Soc. (2005), 127, 1356-1357.
4. Lin, Y. C. and Marra, K. G.; "Indictable systems and implantable conduits for peripheral nerve repair" Biomed Mater (2012), 7(2) doi 024102 (Epub ahead of print).
5. Mawad, D. et al.; "Advances in hydrogels applied to degenerative diseases" Curr Pharm Des Apr. 18, 2012 (Epub ahead of print).

We claim:
1. A liposomal formulation for ocular drug delivery, the formulation defined as:
(a) comprising liposomes with particle sizes selected from the group consisting of 100 to 200 nm hydrodynamic diameters;
(b) exhibiting increased percent encapsulation of drugs into the liposomes compared to encapsulation using a standard, not modified, liposomal formulation; and
(c) comprising a cocktail of at least three different liposomal formulations with hydrophobic anti-oxidants encapsulated within the lipid bilayers, wherein the hydrophobic antioxidants are selected from the group consisting of beta carotene and canthaxanthin, and comprising PC:PE:PG:Cholesterol in varying ratios to customize releasing drugs in timed release from 40 to 200 days the ratios selected from the group consisting of 60:10:0:30; 65:5:5:25 and 60:5:5:30.
2. The drug of claim 1 selected from the group consisting of anti-VEGF antibodies, Bevacizumab (Avastin), Ranibizumab (Lucentis), Pegaptanib (Macugen), Aflibercept (Eylea), Atropine, Flurbiprofen, Physostimine, Azopt, Gentamicin, Pilocarpine, Bacitracin, Goniosol, Polymyxin B, Betadine, Gramicidin, Prednisolone, Betaxolol, Humorsol, Proparacaine, Betoptic, Hylartin, Propine, Brinzolamide, Hypertonic NaCl, Puralube, BSS, Indocycanine Green, Rose Bengal, Carbachol, Itraconazole, Sodium Hyaluronate, Cefazolin, Latanoprost, Suprofen, Celluvisc, Mannitol, Terramycin, Chloramphenicol, Methazolamide, Timolol, Ciloxan, Miconazole, Tobramycin, Ciprofloxacin, Miostat, Triamcinolone, Cosopt, Muro 128, Trifluridine, Demecarium, Neomycin, Tropicamide, Dexamethasone, Neptazane, Trusopt, Dipivefrin, Ocuflo, Vidarabine, Dorzolamide, Ofloxacin, Vira-A, Epinephrine, Oxytetracycline, Viroptic, Fluorescein, Phenylephrine and Xalatan, and combinations thereof.
3. The formulation of claim 1 further comprising a coating wherein the surface of the liposomes are modified by PEGylation to improve stability.

* * * * *